(12) United States Patent
Callewaert et al.

(10) Patent No.: US 7,335,512 B2
(45) Date of Patent: *Feb. 26, 2008

(54) MARKER FOR MEASURING LIVER CIRRHOSIS

(75) Inventors: Nico L. M. Callewaert, Lichtervelde (BE); Roland H. Contreras, Merelbeke (BE)

(73) Assignees: Vlaams Interubiversitair Instituut voor Biotechnologie vzw, Zwijnaarde (BE); Universiteit Gent, Gent (BE)

( * ) Notice: Subject to any disclaimer, the term of this patent is extended or adjusted under 35 U.S.C. 154(b) by 155 days.

This patent is subject to a terminal disclaimer.

(21) Appl. No.: 10/968,579

(22) Filed: Oct. 18, 2004

(65) Prior Publication Data

US 2005/0112691 A1    May 26, 2005

Related U.S. Application Data

(63) Continuation of application No. PCT/EP03/04041, filed on Apr. 16, 2003.

(30) Foreign Application Priority Data

Apr. 16, 2002    (EP) .................................. 02076501

(51) Int. Cl.
*G01N 33/00*    (2006.01)
*C08B 37/00*    (2006.01)

(52) U.S. Cl. ............................ 436/94; 436/63; 436/93; 536/53

(58) Field of Classification Search .................. 436/63, 436/93–95; 435/7.1; 536/53
See application file for complete search history.

(56) References Cited

U.S. PATENT DOCUMENTS 5,831,037 A    11/1998    Ohsuga et al.

FOREIGN PATENT DOCUMENTS

| DE | 38387 18 A1 | 6/1989 |
|---|---|---|
| EP | 0 503 886 A1 | 3/1992 |
| EP | 0 698 793 A2 | 2/1996 |
| WO | WO93/10450 | 5/1993 |
| WO | WO 01/92890 A1 | 12/2001 |
| WO | WO 03/087833 A2 | 10/2003 |

OTHER PUBLICATIONS

Naitoh et al. Journal of Gastroenterology and Hepatology, vol. 14, 1999, pp. 436-445.*
Biou et al., Alterations in the carbohydrate moiety of alpha-l-acid glycoprotein purified from human cirrhotic ascitic fluid, Biochimica et Biophysica Acta, 1987, pp. 308-312, vol. 913.
Giardina et al., Serum alpha-L-Fucosidase Activity and Early Detection of Hepatocellular Carcinoma, Cancer, Dec. 15, 1998, pp. 2468-2474, vol. 83, No. 12.
Matsumoto et al., Alteration of asparagine-linked glycosylation in serum transferrin of patients with hepatocellular carcinoma, Clinica Chimica Acta, 1994, pp. 1-8, vol. 224.
PCT International Search Report, PCT/EP03/04041, dated Mar. 18, 2004.
PCT International Preliminary Examination Report, PCT/EP03/04041, dated Aug. 6, 2004.
Sunayama et al., Elevated plasma levels of a carbohydrate antigen, sialyl Lewis X, in liver diseases, Journal of Hepatology, 1994, pp. 451-458, vol. 19.
Takahashi et al., Comparative Structural Study of the N-Linked Oligosaccharides of Human Normal and Pathological Immunoglobulin G, Biochemistry, 1987, pp. 1137-1144, vol. 26.
Tsutsumi et al., Usefulness of microheterogeneity of serum alpha-l-acidglycoprotein as a marker for alcohol abuse, Alcohol, 2001, pp. 181-184, vol. 25.
Callewaert et al., "Noninvasive diagnosis of liver cirrhosis using DNA sequencer-based total serum protein glycomics", *Nature Medicine*, 2004, vol. 10, 429-434.
Field et al., "Structural analysis of the N-glycans from human immunoglobulin Al: comparison of normal human serum immunoglobulin Al with that isolated from patients with rheumatoid arthritis", *Biochem. J.*, 1994, vol. 299, 261-275.
Wang et al., "Analysis of the characteristics of microheterogeneity of various serum glycoproteins in chronic alcoholics", *Alcohol Alcohol Suppl.*, 1993, 1A, 21-28.

* cited by examiner

*Primary Examiner*—Maureen M. Wallenhorst
(74) *Attorney, Agent, or Firm*—TraskBritt

(57) ABSTRACT

The invention provides methods and kits to detect liver cirrhosis in mammals. The diagnostic test is based on the profiling and identification of diagnostic carbohydrates present in a body fluid such as blood serum.

10 Claims, 9 Drawing Sheets

Figure 1:
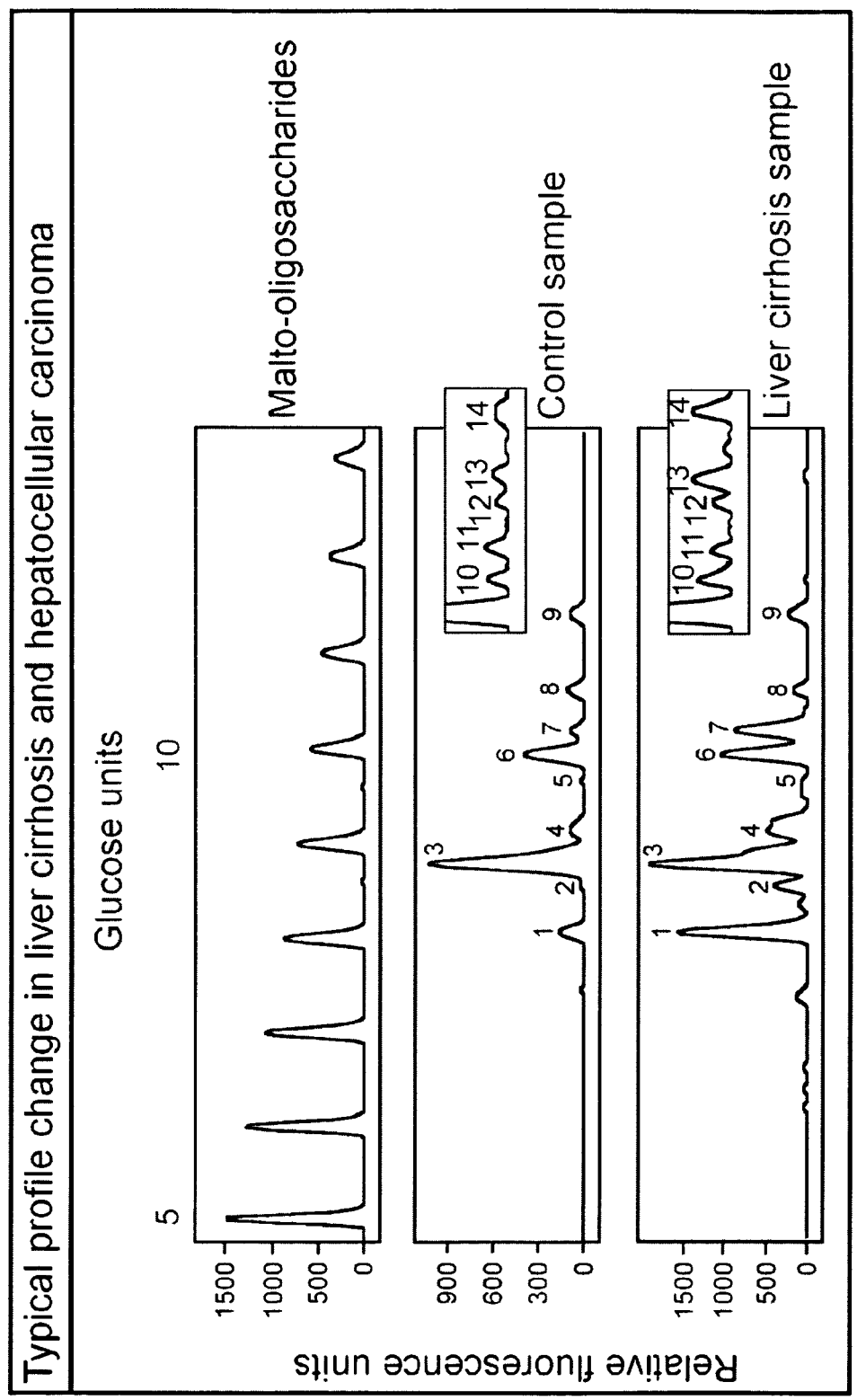

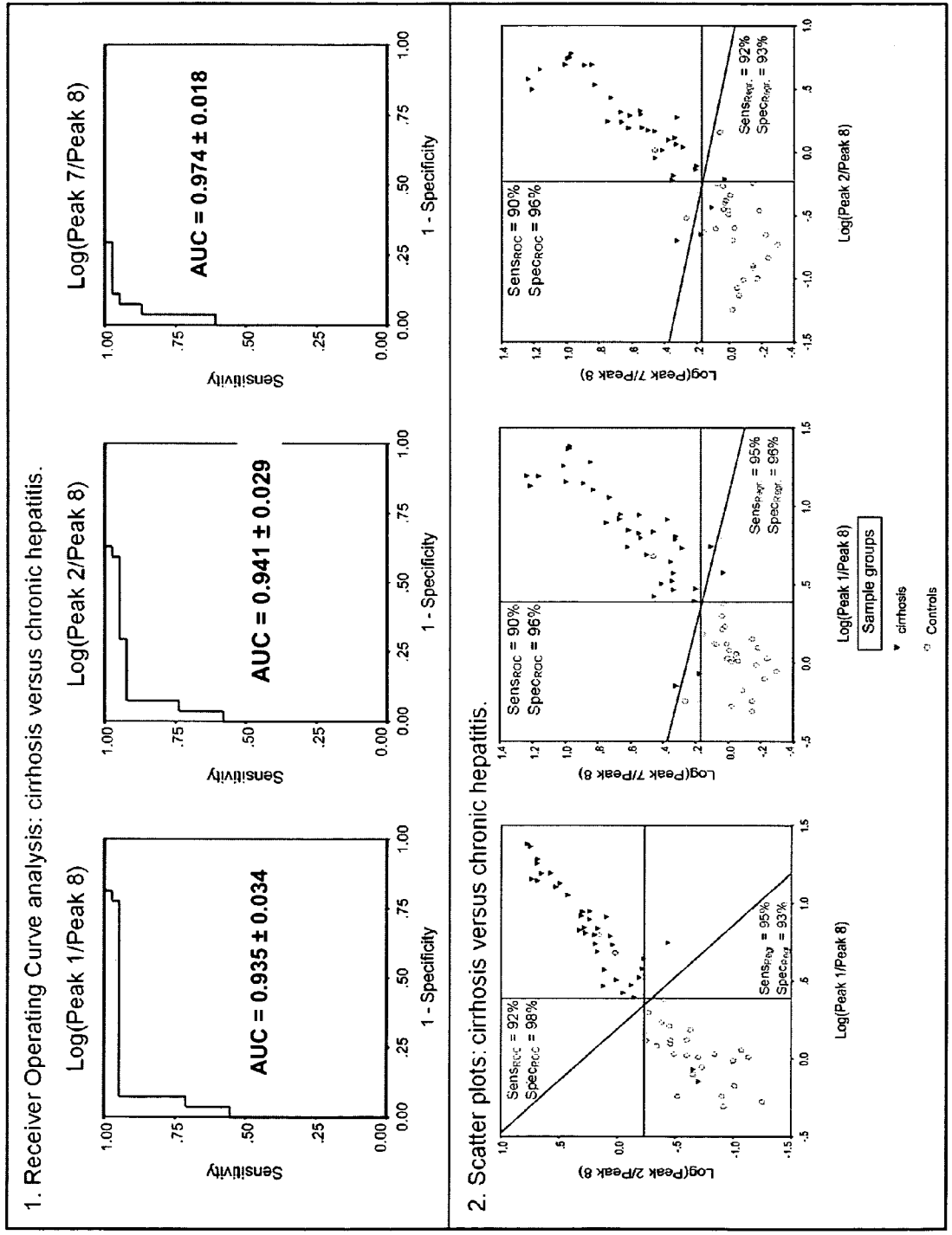
FIG. 3 (part 1)

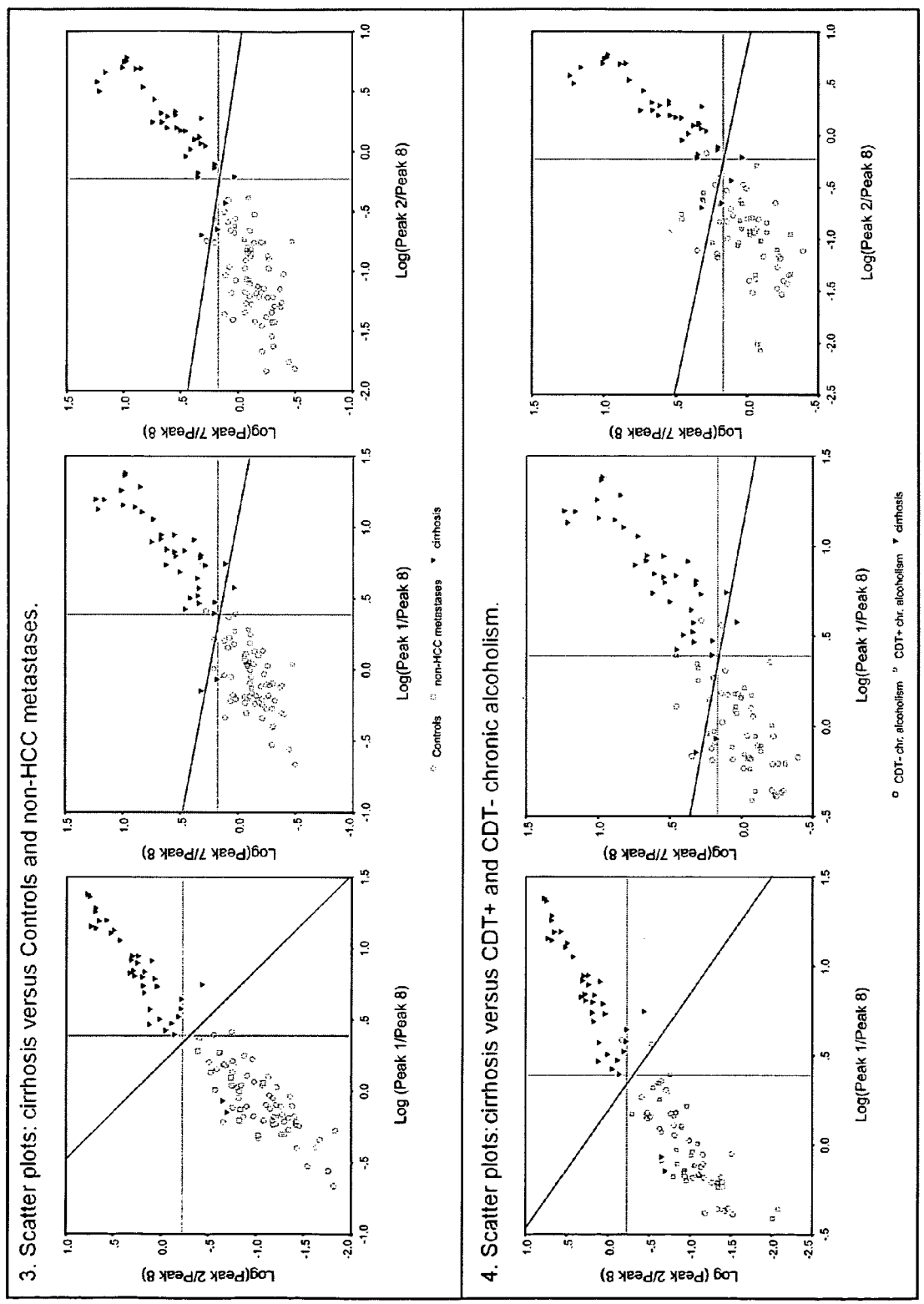
FIG. 3 (part 2)

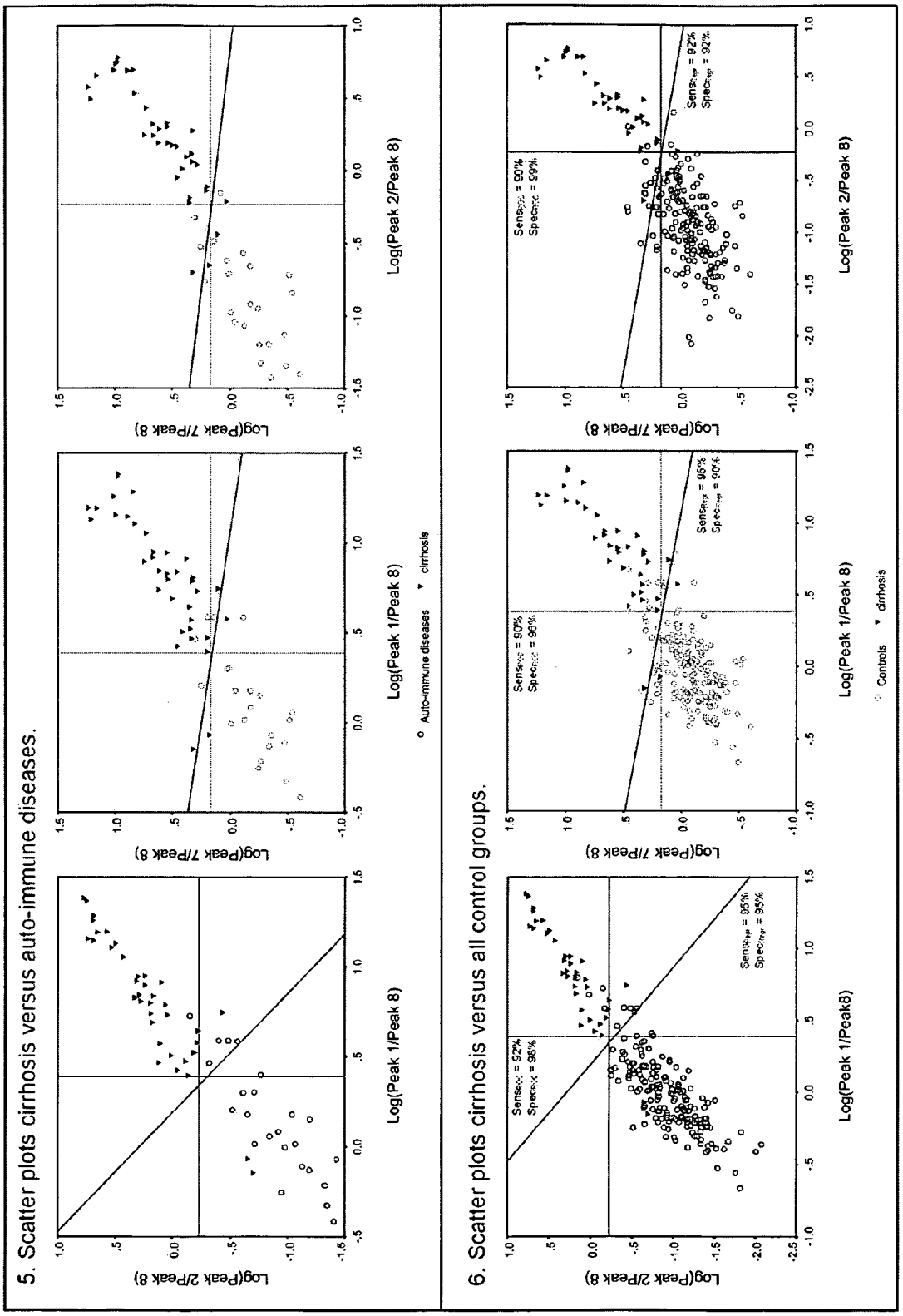
FIG. 3 (part 3)

7. ROC curves: glycomics cirrhosis marker versus albumin and bilirubin
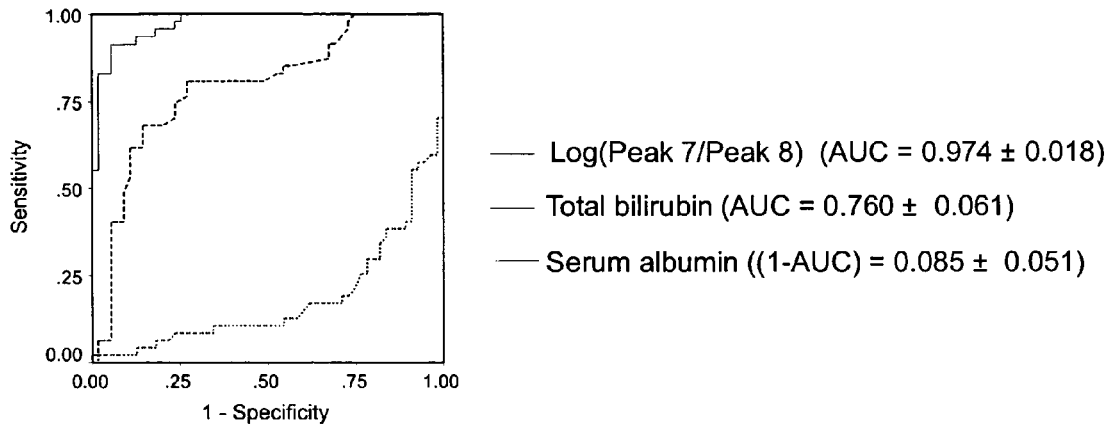
8. Classification validation in independent group of liver disease patients
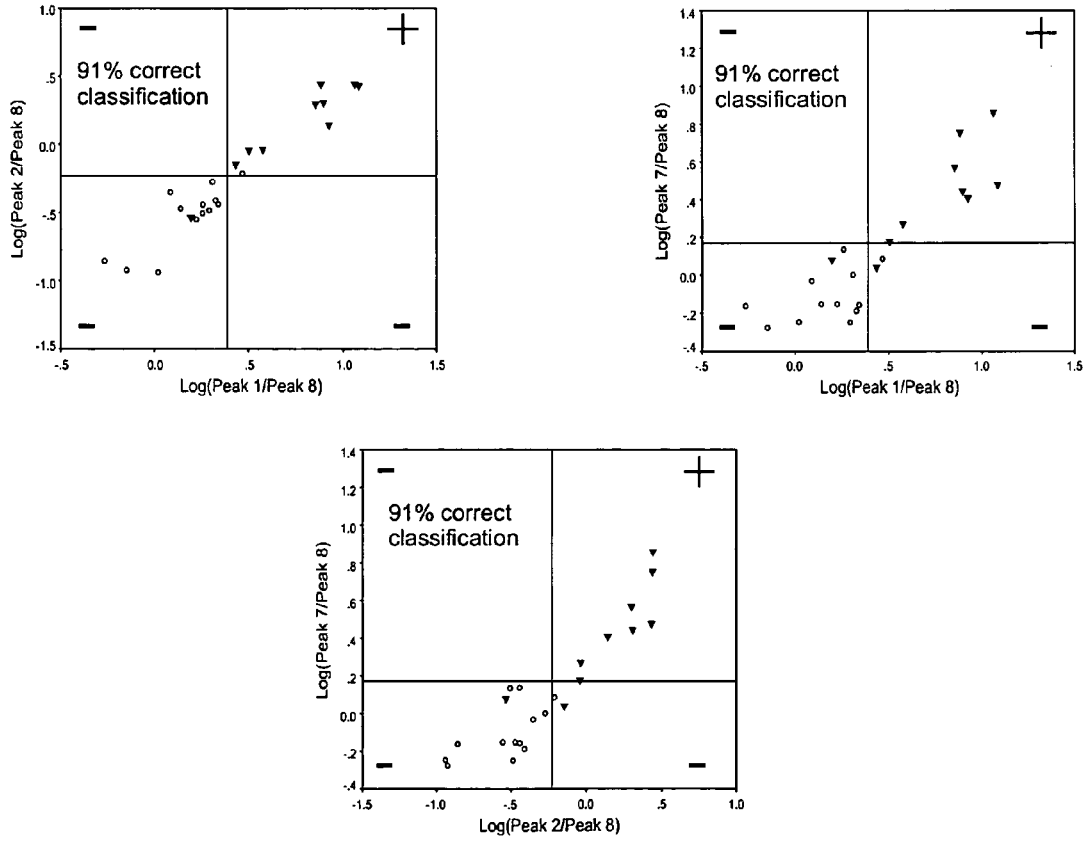
FIG. 3 (part 4)

MARKER FOR MEASURING LIVER CIRRHOSIS

CROSS-REFERENCE TO RELATED APPLICATIONS

This application is a continuation of co-pending International Application No. PCT/EP03/04041 filed Apr. 16, 2003, designating the United States of America, corresponding to International Publication No. WO 03/087833, published in English on Oct. 23, 2003, the contents of which are incorporated herein in their entirety.

TECHNICAL FIELD

The invention relates generally to biotechnology and medicine, and generally provides methods, tests, and kits to detect liver cirrhosis in mammals. The diagnostic test is based on the profiling and identification of diagnostic carbohydrates present in a body fluid such as blood serum.

BACKGROUND

Most of the common causes of liver injury result in cirrhosis. Cirrhosis is the destruction of normal liver tissue that leaves non-functioning scar tissue surrounding areas of functioning liver tissue, accompanied with the formation of regenerative liver nodules. In the United States, the most common cause of cirrhosis is alcohol abuse. Among people ages 45 to 65, cirrhosis is the third most common cause of death, after heart disease and cancer. In many parts of Asia and Africa, chronic hepatitis is a major cause of cirrhosis. Many people with mild cirrhosis have no symptoms and appear to be well for years. Others are weak, have a poor appetite, feel sick, and lose weight. If bile flow is chronically obstructed, the person has jaundice, itching, and small yellow skin nodules, especially around the eyelids. Malnutrition commonly results from a poor appetite and the impaired absorption of fats and fat-soluble vitamins caused by the reduced production of bile salts. Occasionally, the person may cough up or vomit large amounts of blood because of bleeding from varicose veins at the lower end of the esophagus (esophageal varices). These enlarged blood vessels result from high blood pressure in the veins that run from the intestine to the liver. Such high blood pressure, called portal hypertension, along with poor liver function, may also lead to fluid accumulation in the abdomen (ascites). Kidney failure and liver encephalopathy also may develop. Other symptoms of long-standing liver disease may develop, such as muscle wasting, redness of the palms (palmar erythema), a curling up of the fingers (Dupuytren's contracture of the palms), small spider-like veins in the skin, breast enlargement in men (gynecomastia), salivary gland enlargement in the cheeks, hair loss, shrinking of the testes (testicular atrophy), and abnormal nerve function, both in the periphery (peripheral neuropathy) and in the central nervous system.

At present, no cure exists for cirrhosis. Treatment includes withdrawing toxic agents such as alcohol, receiving or providing proper nutrition including supplemental vitamins, and treating complications as they arise. Liver transplantation is presently the only cure, and may help a person with advanced cirrhosis. Moreover, the presence of cirrhosis increases the risk of developing hepatocellular carcinoma to about 40-fold over the risk in the general population and, in an etiological background of chronic hepatitis and alcoholism, the development of cirrhosis multiplies the already increased risk to the patient of developing hepatocellular carcinoma from 34.4 to 119-fold and from 2.4 to 22.4-fold, respectively (Kuper et al., 2001). Usually, a number of blood tests are performed to measure liver function and to help determine the severity and cause of cirrhosis. One of the most important factors indicative of liver damage is bilirubin, a red-yellow pigment that is normally metabolized in the liver and then excreted in the urine. In patients with hepatitis, the liver cannot process bilirubin, and blood levels of this substance rise, sometimes causing jaundice.

The levels of certain liver enzymes can also be indicative for cirrhosis (e.g., aspartate and alanine aminotransferase levels and several clotting enzymes). However, results of these liver function tests often are normal because only a small percentage of functioning liver cells are needed to carry out essential chemical functions. In addition, a number of imaging tests are used to diagnose possible cirrhosis and its complications. For example, an ultrasound scan may show that the liver is enlarged and that particular lesions, such as regenerative nodules, are present. Other, much more costly, imaging techniques are magnetic resonance imaging (MRI) and computed tomography (CT). In most of the patients presenting with some form of chronic liver disorder, liver biopsy is performed to assess the degree of fibrosis and to detect the presence of cirrhosis (Fracanzani et al., 2001). As liver biopsy is an invasive procedure, it is generally difficult to perform it on a regular follow-up basis in the normal clinical setting. A specific serum marker for the detection of liver cirrhosis could thus have a very significant impact on gastroenterology practice, in allowing regular follow-up of chronic liver disease patients, and in providing early warning for the onset of cirrhosis. In the particular case of chronic alcoholism, a serum marker for cirrhosis could provide an important argument to convince the patient to stop drinking.

Measurement of diagnostic glycans in carbohydrate metabolism diseases is described in the art (PCT International Publication No. WO9219975). In the field of hepatic disorders, it is also known that single glycosylation enzyme activities are altered in liver disorders. For example an increased activity of the enzyme UDP-N-acetyl-glucosamine:glycoprotein N-acetyl-glucosaminyl-transferase (GnTIII) is correlated with the progression of liver disease (Ishibashi et al., 1989), a finding that has recently been elaborated upon in a diagnostic setting (Mori et al., 1998). However, these assays are complicated by the HPLC separation of the products of the enzymatic reaction. Moreover, the stability of the enzyme in serum in storage conditions is unknown and the values obtained for serum GnTIII activity have large overlaps between cirrhosis and chronic hepatitis. Glycosylation differences have also been studied on a purified protein, serum transferrin, and these differences are used for the detection of chronic alcoholism (Matsumoto K. et al., 1994, *Clin. Chim. Acta* 224(1): 1-8). Alterations in the carbohydrate moiety of single purified proteins have also been described in human cirrhotic ascitic fluid (Biou, D. et al., 1987, Biochimica et Biophysica Acta 913, 308-312). Methods for the detection of liver diseases are described in patents EP0503886 and DE3838718. However, the latter patents deal with the quantification of simple carbohydrates (fucose) in urine.

There is currently no easily measurable, reliable serum marker for the differentiation of liver cirrhosis from other hepatic disorders.

SUMMARY OF THE INVENTION

In the present invention we have identified multiple parameters of diagnostic carbohydrates derived from the pool of proteins present in the serum of cirrhosis patients. In serum, a complex mixture of glycosylated and unglycosylated proteins is present which are derived from liver and plasma cells. Unexpectedly, we have found that (relative) amounts of diagnostic carbohydrates present on a mixture of glycoproteins, that are present in the total serum, serve as a diagnostic marker for the differentiation of liver cirrhosis patients from chronic hepatitis patients and for the differentiation of liver cirrhosis from other non-malignant and malignant hepatic disorders. An advantage of analyzing the pool of total serum glycoproteins is that the amount of work required for sample preparation is reduced to the minimum. This allows the analysis of clinically relevant numbers of patients.

BRIEF DESCRIPTION OF FIGURES AND TABLES

FIG. 1. Profile examples. The upper panel contains a dextran hydrolysate and can be used to assign a glucose unit value to each peak. The second panel shows a typical electropherogram of the N-glycans derived from the proteins in a control serum sample. Nine peaks are clearly visible in this detection range and their height was used to obtain a numerical description of the profiles of all samples in this invention. The third panel shows the electropherogram obtained from a cirrhosis case. The extra peaks 10, 11, 12, 13 and 14 (see insert boxes) only become visible in the electropherogram after a ten-fold higher concentration of N-glycans derived from the proteins from the sera. Several profile alterations are evident and form the basis for the diagnostic marker.

Figure 2:
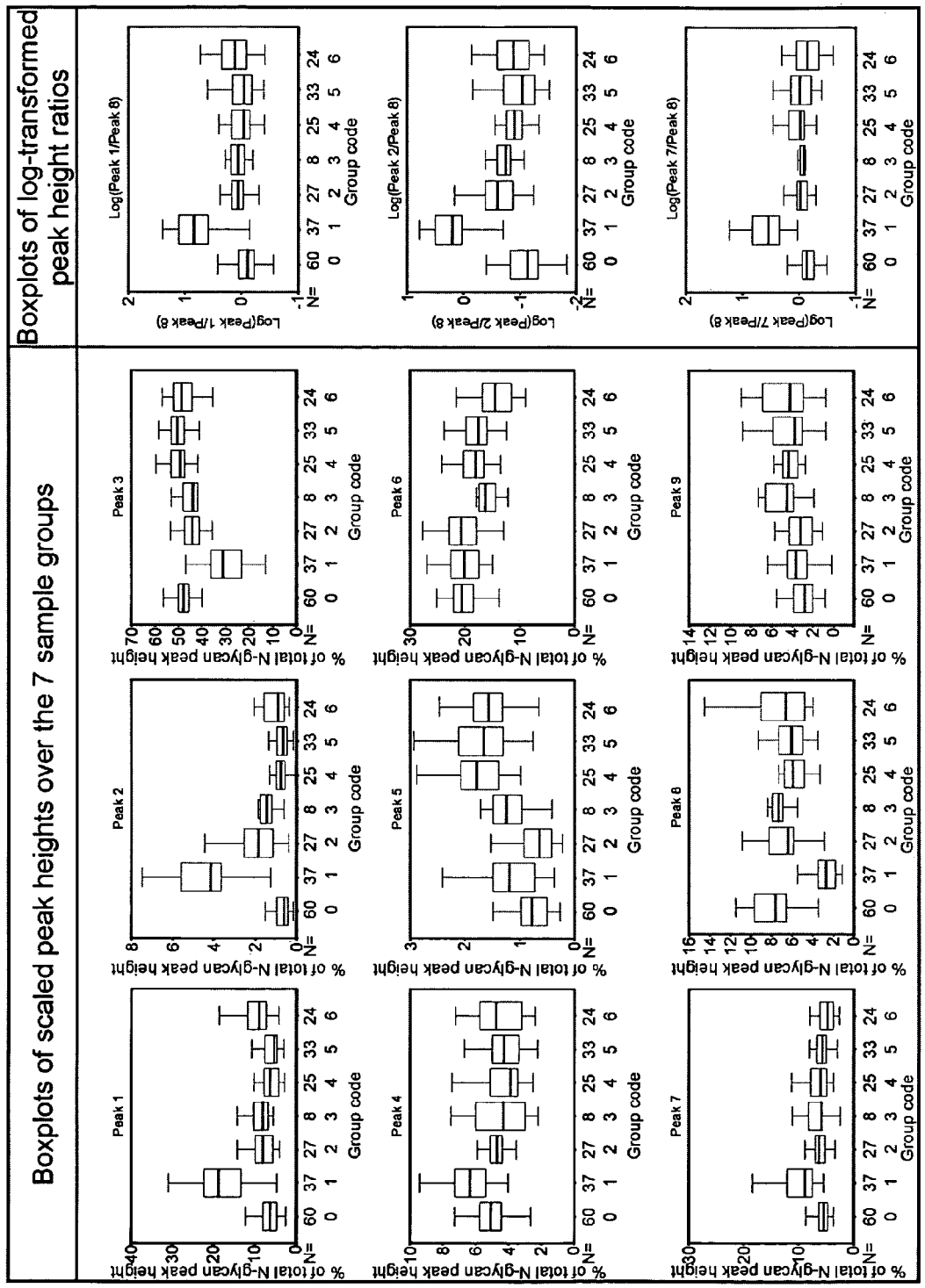

FIG. 2. Box plots summarizing the data. The samples are classified in seven groups (Code 0 to 6) as shown in Table 1, fourth column. For each of the nine peaks, the median of the values in each of these seven groups is represented by the thicker black line and the interquartile ranges are represented by the limits of the boxes and errorbars. For peaks 1, 2, 3, 7 and 8 the inner interquartile ranges of sample group 0 and 2, on the one hand, and group 1, on the other hand, do not overlap. The relative amount between peaks 1, 2, 7 and peak 8 was calculated to create three new variables, the properties of which are summarized in the right column of the figures. Note that the ordinate scale is logarithmic for these three new variables.

FIG. 3. Evaluation of the diagnostic efficiency of the three variables using Receiver Operating Curve (ROC) analysis and binary logistic regression. Section 1: ROC analysis was performed to evaluate the efficiency of the three variables in differentiating the sample group with cirrhosis and the group with chronic viral hepatitis without cirrhosis. The cut-off values determined from these ROC curves (optimal combined sensitivity and specificity) were used in the subsequent sections 2, 3, 4, 5 and 6 of this FIG. to divide the two-dimensional scatterplot fields in quadrants (the top right quadrant being the positive quadrant for liver cirrhosis, and the other three quadrants constituting the negative area). The regression line obtained from binary logistic regression analysis, with each time two variables as independents, is also shown in these scatterplots. The cirrhosis sample group is shown in each scatterplot as black triangles. The "negative" group in each section is represented with either circles or squares. Section 7: a comparison was made by ROC analysis of the classification efficiency between the sample group with cirrhosis and the group with chronic viral hepatitis without cirrhosis, for the variable Log (Peak 7/Peak 8) and serum albumin concentration and total serum bilirubin concentration. The result shows that the serum N-glycan profile-derived marker has an approximately 5-fold reduction in the rate of misclassified cases (approximately 1 in 25, versus approximately 1 in 4 (bilirubin), or 1 in 5 (albumin)). Section 8: to validate the ROC-derived cut-off values for the serum N-glycan profile derived markers, these values were used to classify a second, independent group of chronic hepatitis patients with or without cirrhosis. Very similar classification efficiencies were obtained in this second group as were obtained in the optimization group (see Section 2 of the FIG.).

Figure 4:
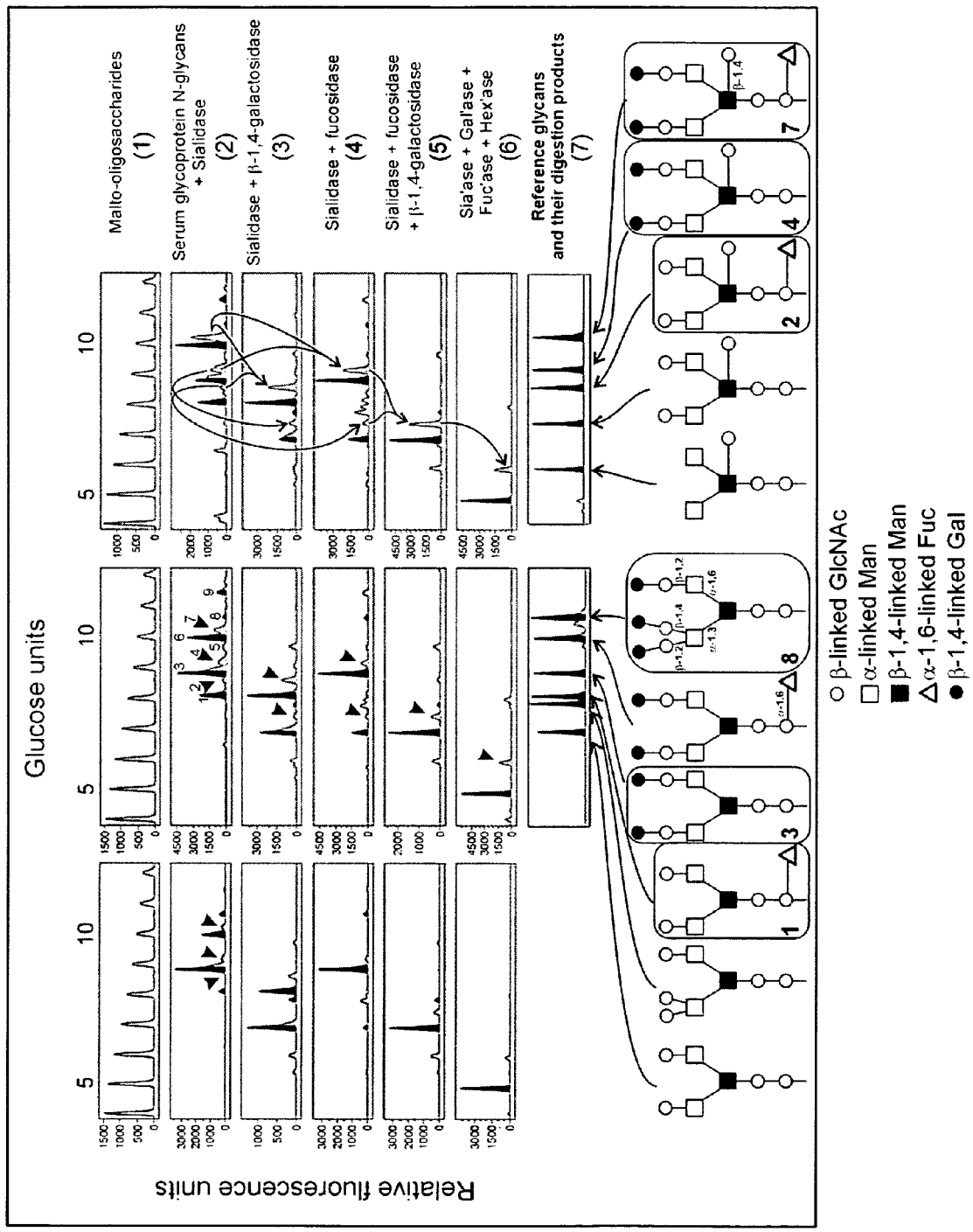

FIG. 4. Partial structural analysis of the differentially regulated N-glycans. The three columns in this FIG. represent the results of exoglycosidase array sequencing on the N-glycans derived from the glycoproteins in three serum samples. These samples were chosen to reflect the quantitative range of the observed alterations in this study. The leftmost sequencing column was obtained from analysis of a sample with chronic hepatitis and is indistinguishable from a healthy control's profile. The middle column represents a mild alteration, already trespassing the cut-off values for all three variables described in the text. The right column results from analysis of one of the worst affected samples. It is useful to compare the peaks described in the text over these three columns, and the possibility for this comparison greatly simplifies the peak tracking throughout the exoglycosidase sequencing panels. The peaks depicted in black do not bear a bisecting GlcNAc residue. In this respect, they can all be regarded as derivatives of the trimannosyl-GlcNAc$_2$ core oligosaccharide. The peaks depicted in grey were found to be all modified with a bisecting GlcNAc residue and thus can all be considered as derivatives of the bisecting GlcNAc-substituted trimannosyl-GlcNAc$_2$ core oligosaccharide. The reference panel under the middle sequencing column was assembled from six different electropherograms, each containing a specific exoglycosidase digest on reference glycans with known structure. The reference glycans used were: 1) trisialo, trigalacto triantennary, 2) bisialo, bigalacto biantennary with core-α-1,6-linked fucose (Reference panel under middle column) and 3) asialo, bigalacto biantennary with core-α-1,6-linked fucose and bisecting GlcNAc (see, reference panel under rightmost column).

Figure 5:
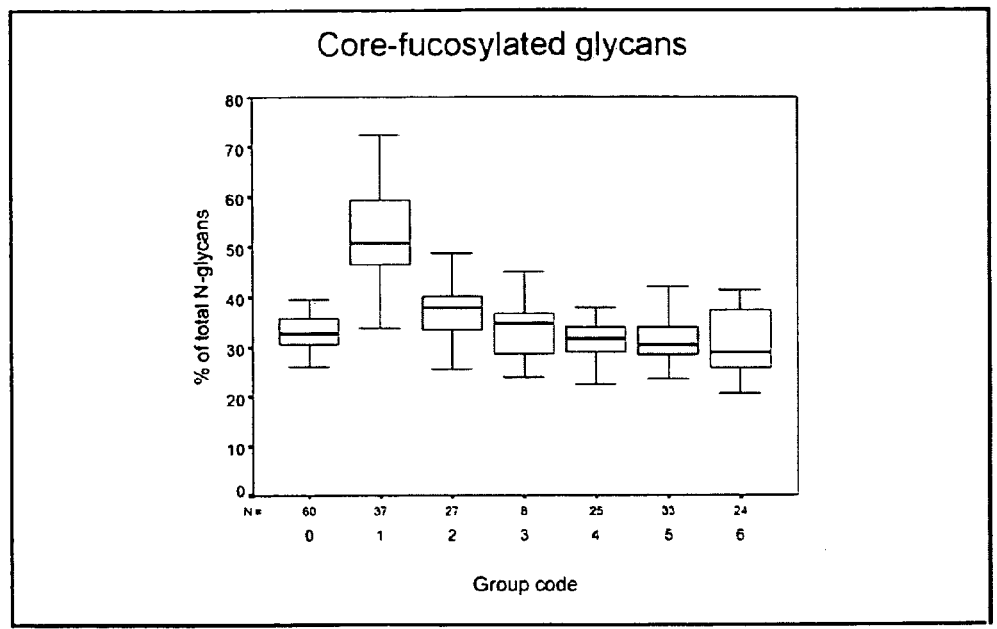

FIG. 5. Characteristics of the core-fucosylation variable. To evaluate whether core-α-1,6-fucosylation was increased in the cirrhosis group, a new variable was created by summation of the normalized peak heights of all identified peaks that carry this modification. A boxplot visualization analogous to those in FIG. 2 is shown, together with the results of ANOVA and subsequent post hoc tests. Again, the cirrhosis group is set aside as a homogenous subgroup, thus confirming the increased core-fucosylation in these disorders.

Figure 6:
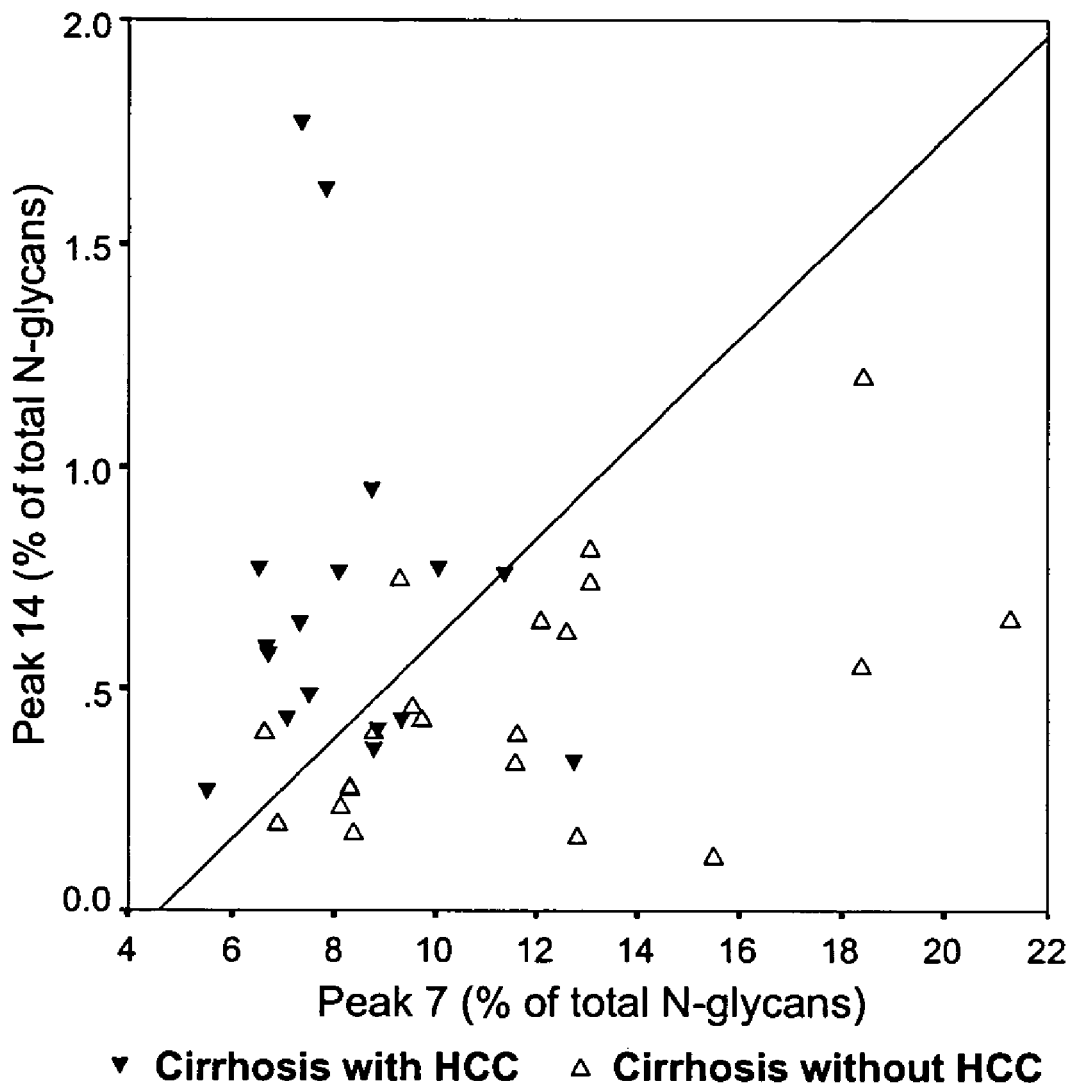

FIG. 6. Discrimination between cirrhosis cases with and without hepatocellular carcinoma. Scatterplot of the cirrhosis cases with and without hepatocellular carcinoma, plotting the height of Peak 7 versus Peak 14 (see FIG. 1), normalized to the total measured peak height in the serum protein N-glycan profile. Cases with only cirrhosis are depicted as empty triangles. Cases with cirrhosis and HCC are depicted as black point-down triangles. Binary logistic regression allowed the identification of cases with HCC with a sensitivity of 71% and a specificity of 90%. The logistic function of the model is: $Z=-0.649[\%$ Peak $7]+5.722[\%$ Peak 14]+2.967. The diagonal line in the FIG. is the cut-off line where each point on the line would be a case with equal probability to belong to either of the two distinguished groups.

DETAILED DESCRIPTION OF THE INVENTION

The study of complex glycans ("glycobiology," Kobata, 2000; Roseman, 2001) is beginning to evolve into a more general approach that might be called glycomics (Hirabayashi et al., 2001; Taniguchi et al., 2001). Analogously to proteomics, glycomics can be defined as the study of the realm of glycans present in all or a particular class of glycoconjugates in a biological sample on a quantitative basis and the comparison of the obtained profiles to derive biological information. On the basic research side, functional glyco(proteo)Mics has the ambition to clarify the roles in a diverse range of physiological processes of the glycan moieties of glycoconjugates by detecting changes in the glycome and subsequently determine the identity of the non-glycan moieties (mostly proteins) that carry the altered glycans. In this respect, it is analogous in its approaches to basic proteomics research but the technologies used are generally too complex and/or time-consuming to find applications outside the basic research laboratories. Especially in the clinical field, where analysis of hundreds of samples is necessary to derive meaningful information, the current glycomics approaches have significant shortcomings due to their complexity. In the present invention we have developed a technology platform for a clinical glycomics application in the detection of liver cirrhosis. We have profiled the carbohydrate structures derived from the glycoproteins present in serum and have identified statistically relevant differences in the glycan profiles between patients suffering from liver cirrhosis and patients free of liver cirrhosis. In other words, amounts of diagnostic carbohydrates or relative amounts between carbohydrates have been identified in the present invention that are correlated with the presence of liver cirrhosis. The profiling of carbohydrates used in the diagnostic test for liver cirrhosis of the present invention can for example be carried out with an Applied Biosystems 377 gel-based DNA-sequencer (Callewaert et al., 2001).

Thus, with the diagnostic method of the present invention it is possible to reliably differentiate patients with liver cirrhosis and liver cirrhosis complicated with hepatocellular carcinoma from (1) healthy donors, (2) patients suffering from chronic hepatitis B or C, (3) patients suffering from rheumatoid disorders, (4) patients with a suspected chronic alcohol abuse and (5) patients with non-HCC metastases to the liver. In addition, the diagnostic method of the invention can also diagnose a predisposition or presence of hepatocellular carcinoma (HCC) in a background of liver cirrhosis. We were able to differentiate patients with cirrhosis from the five groups mentioned above with sensitivities and specificities that were never below 90% and in the most relevant diagnosis (distinction between cirrhosis and healthy volunteers and the distinction between cirrhosis and patients suffering from chronic hepatitis) the values for sensitivity and specificity were higher than 95%.

As there is currently no easily measurable and specific serum diagnostic marker for cirrhosis, the usage of this non-invasive diagnostic test can include the guidance of therapeutic decisions in the treatment of cirrhosis (currently only liver transplantation is a cure), the closer monitoring of cirrhosis-positive patients for the development of hepatocellular carcinoma and the evaluation of the extent of liver damage in a patient presenting with symptoms of chronic alcohol consumption. This serum marker for cirrhosis can also be used to non-invasively measure the rate of conversion to cirrhosis of patients chronically infected with the hepatitis C virus in vaccine clinical trials, as a reduced incidence and/or a retardation of the onset of liver cirrhosis constitutes an important clinical endpoint which is currently very difficult to assess because of the necessity of invasive biopsy techniques.

In a first embodiment, the invention provides a method to detect liver cirrhosis in a mammal, comprising (a) generating a profile of carbohydrates or fragments derived thereof, or labeled derivatives of carbohydrates or fragments, or features of carbohydrates or carbohydrate fragments that are determined by the structure of carbohydrates or carbohydrate fragments; the carbohydrates or fragments being present on or obtained from a mixture of glycoconjugates that are present in or are isolated from a sample of a body fluid from a mammal, and (b) measuring in the profile generated in step (a) the amount of at least one carbohydrate or a fragment derived thereof or a labeled derivative of the carbohydrate or fragment, or a feature of at least one carbohydrate or fragment derived thereof present in the carbohydrate profile, and (c) comparing the measured data obtained in step (b) with measured data obtained from profiles derived from mammals free of liver cirrhosis, and (d) attributing the deviation obtained in step (c) to liver cirrhosis. The wording "a method to detect liver cirrhosis" can be broadly understood as a method for screening, a method for diagnosis or a method for prognosing liver cirrhosis.

In another embodiment, a carbohydrate profile is used for the manufacture of a diagnostic assay for the detection of liver cirrhosis. The diagnostic assay comprises the following steps (a) generating a profile of carbohydrates or fragments derived thereof, or labeled derivatives of carbohydrates or fragments, or features of carbohydrates or carbohydrate fragments that are determined by the structure of carbohydrates or carbohydrate fragments; the carbohydrates or fragments being present on or obtained from a mixture of glycoconjugates that are present in or are isolated from a sample of a body fluid from a mammal, and (b) measuring in the profile of step (a) the amount of at least one carbohydrate or a fragment derived thereof or a labeled derivative of the carbohydrate or fragment, or a feature of at least one carbohydrate or fragment derived thereof present in the carbohydrate profile, and (c) comparing the measured data obtained in step (b) with measured data obtained from profiles derived from mammals free of liver cirrhosis, and (d) attributing the deviation obtained in step (c) to liver cirrhosis.

In another embodiment, the invention provides a method to detect liver cirrhosis in a mammal, comprising: (a) generating a profile of carbohydrates or fragments derived thereof, or labeled derivatives of carbohydrates or fragments, or features of carbohydrates or carbohydrate fragments that are determined by the structure of carbohydrates or carbohydrate fragments; the carbohydrates or fragments being present on or obtained from a mixture of glycoconjugates that are present in or are isolated from a sample of a body fluid from a mammal, and (b) comparing quantitative or qualitative aspects of the profile to the quantitative or qualitative aspects of such a profile obtained from one or more individuals of a mammalian species.

The wording "glycoconjugates that are present in" refers to carbohydrates which are detected on the glycoconjugates without any isolation step of carbohydrates; thus the sample is used as such and does not imply any isolation step of the carbohydrates, whereas the wording "or are isolated from a sample of a body fluid" refers to the fact that the carbohydrates are isolated from the glycoconjugates present in the sample.

In a particular embodiment, the method of the invention can be used for monitoring the effect of therapy administered to a mammal suffering from liver cirrhosis. In another particular embodiment the method of the invention specifically detects liver cirrhosis. The term "specifically" refers to the fact that liver cirrhosis can be diagnosed differently from other hepatic disorders such as hepatitis B or C infection.

The term "carbohydrate" can be understood as glycans that are present in the structure of or that are derived from glycoconjugates, comprising the glycan categories known in the art as asparagine-linked glycans (also designated as N-glycans) or Serine/Threonine-linked glycans (also designated as O-glycans) of proteins or glycosaminoglycans or proteoglycan derived glycans, glycans present in or derived from glycolipids and GPI-anchor derived carbohydrates. The words "glycan" and "carbohydrate" are interchangeable. A "glycoconjugate" means any compound (e.g., protein or lipid) containing a carbohydrate moiety. The phrase, "a mixture of glycoconjugates," means a composition containing at least two (including at least three, at least four, at least five or more) of the glycoconjugates, potentially also comprising non-glycoconjugate materials such as proteins, lipids, salts and water. The wording "carbohydrates or fragments derived thereof" means that carbohydrates can be fragmented to yield at least one oligosaccharide or a derivative thereof amongst the products of the fragmentation process. Other products of this fragmentation process might include monosaccharides and oligosaccharides or derivatives thereof. An oligosaccharide is a carbohydrate of which the chemical structure consists of at least two chemically linked units known in the art as monosaccharide. The fragmentation process can involve enzymatic, chemical, and physical treatments. For example, carbohydrates can be treated (or digested) with a glycosidase enzyme (e.g., a sialidase to remove the sialic acid residues from the carbohydrates, or a fucosidase to remove fucose residues from the carbohydrates) and therefore the profile obtained consists of fragments of the carbohydrates. Glycosidase digestions can for example be carried out to obtain a more simple profile of the carbohydrates. Sialic acids may also be removed in a chemical way by mild acid hydrolysis of the carbohydrates. In mass spectrometric (MS) analysis methods, the word "fragments" refers to the fact that carbohydrates are very often fragmented in the process of analysis (for example in collision induced dissociation), in which case the fragmentation products can also yield an oligosaccharide derivative made up of an oligosaccharide chemically linked to the remnant of one or more monosaccharides that were part of the structure of the carbohydrate before fragmentation took place. An example of such an oligosaccharide derivative being the product of a MS fragmentation process is known in the art as a cross-ring cleavage product ion. A "feature of the carbohydrate" refers to any measurable parameter of which the properties and/or the quantity is determined by the structure of the carbohydrate. Examples of such measurable parameters are for example nuclear magnetic resonance parameters such as chemical shifts, homonuclear and heteronuclear coupling constants, Nuclear Overhauser Effects and residual dipolar couplings. Alternatively, such measurable parameters might be the extent of binding to the carbohydrate to other molecules such as lectins and antibodies that recognize specific structural determinants or combinations thereof in the carbohydrate. Yet other such measurable parameters might be the extent of the capacity of the carbohydrate to function as a substrate for an enzyme that specifically modifies certain carbohydrates such as glycosyltransferases and glycosidases.

The wording "carbohydrates or fragments being present on or obtained from a mixture of glycoconjugates" refers to the fact that a "profile of carbohydrates of fragments derived thereof or labeled derivatives of carbohydrates or fragments, or features of carbohydrates or carbohydrate fragments that are determined by the structure of carbohydrates or carbohydrate fragments" can be either obtained from carbohydrates that are still chemically linked to the glycoconjugates in the mixture, or from carbohydrates that have been released from the glycoconjugates by enzymatic, chemical or physical means. In a preferred embodiment, N-glycans are released from the glycoproteins in the mixture by enzymatic digestion with Peptide N-glycosidase F or other endoglycosidases known in the art. In another embodiment, N-and O-glycans can be released using a procedure involving hydrazine, known to those skilled in the art. In yet another embodiment, O-glycans can be selectively released using beta elimination in alkaline conditions according to well-known procedures. In case the profile is obtained on carbohydrates that are still chemically linked to the glycoconjugates in the mixture, one embodiment involves the use of enzymes or chemical procedures to modify the non-glycan part of the glycoconjugate prior to obtaining the profile, such as proteases or enzymes which modify the lipid part of glycolipids. The wording "a profile of carbohydrates" means any entity comprising qualitative and/or quantitative information on carbohydrates. For example, this may mean an electrophoretic or chromatographic profile of carbohydrates. In a particular case, the profile is a mass spectrum of carbohydrates. Alternatively, the profile can be information obtained by Nuclear Magnetic Resonance analysis. In yet another example, the profile can be information describing qualitative or quantitative aspects of lectin binding to the carbohydrates. Alternatively, the profile can be information describing the extent to which the carbohydrates are substrates for specific enzymes such as glycosyltransferases or glycosidases. Such information can include read-outs of measurements of by-products of such enzymatic reactions, such as nucleotides set free in equimolar amounts in glycosyltransferase reactions. In a particular embodiment the wording "generating a profile of carbohydrates" or "profiling of carbohydrates" also can imply that the glycan structures are separated and subsequently detected. Usually a number of carbohydrates are identified in a profile of carbohydrates. Usually the carbohydrates are present in a complex mixture and separation is necessary for an efficient detection. Separation can be carried out with methods comprising electrophoretic and chromatographic methods. Detection can be carried out with methods including, but not limited to, antibody detection, lectin detection, NMR, MS and fluorescence. In a particular embodiment it is necessary to chemically and/or enzymatically remove the glycans from the glycoproteins before the glycans can be profiled. Methods to prepare glycans from glycoproteins are well known in the art. In another particular embodiment it is necessary to derivatize the glycans before the separation and the detection. In one approach the method of the present invention for the profiling (includes separation and detection) of glycans can be carried out in combination with a DNA-sequencer. However, it is clear for the person skilled in the art that this method can also be applied in connection with capillary electrophoresis systems adaptable to a laser induced fluorescence detector. Such systems for instance include the P/ACE series Capillary Electrophoresis Systems (Beckman Instruments, Inc., Fullerton, Calif.). The invention can also be applied using any electrophoresis system which is adaptable with a laser induced fluorescence detector. In another embodiment also MS detection methods can be used such as MALDI-TOF-MS for the measurement of the amount of at least one carbohydrate or a fragment derived thereof. In MS methods, the carbohydrates are often fragmented and therefore, in these methods, fragments of carbohydrates are detected.

In yet another embodiment, the profiling can be carried out with a microfluidics method. Microfluidics is a rapidly growing field and is based on fluid migration through narrow-bore channels created in a solid medium (mostly silica wafers or high-purity glass plates) via techniques borrowed from the microchip industry (photolithography and chemical wet etching). Fluids can migrate through these channels via capillary action or active pumping, and analytes can migrate in fluid-filled channels through electrophoresis (Schmalzing et al., 2001, *Methods Mol. Biol.* 163, 163-173). In yet another embodiment, the separation of carbohydrates can be carried out via a chromatographic separation with methods including thin layer chromatography (TLC), high performance liquid chromatography or gas chromatography.

The term "at least one carbohydrate" refers to the measurement of the amount of at least one carbohydrate present in the carbohydrate profile that is diagnostically relevant for the detection of liver cirrhosis ("at least one carbohydrate" can therefore be designated as an at least one diagnostic carbohydrate). In one embodiment the measurement of one carbohydrate is sufficient to diagnose liver cirrhosis. This means that in one example, one carbohydrate is present in a mammal suffering from cirrhosis and is absent in a mammal free of cirrhosis. In another example, one carbohydrate is present in a mammal free of cirrhosis and absent in a mammal suffering from cirrhosis. In another particular example, a different amount of one carbohydrate is sufficient to differentiate between a mammal suffering from cirrhosis and a mammal free of cirrhosis. In a preferred embodiment, the amount of one, two or even more (diagnostic) carbohydrates is measured. In a profiling method, the amount of the (diagnostic) carbohydrate can, for example, be measured by calculating the peak height or the peak surface. By comparing the amount of at least one (diagnostic) carbohydrate, present in patient samples, with corresponding diagnostic carbohydrate levels present in an individual free of liver cirrhosis, the presence or absence of liver cirrhosis can be diagnosed. The invention can be used on samples obtained from mammals, such as humans. Diagnostic carbohydrates may be oligosaccharides or polysaccharides. Diagnostic carbohydrates may be branched or unbranched. Diagnostic carbohydrates in a sample from an afflicted individual with liver cirrhosis are present with an abundance (amount) that is either consistently higher or consistently lower than in a sample from an unafflicted individual (not having liver cirrhosis).

The term "labeled derivatives of carbohydrates or fragments" refers to carbohydrates that have been labeled with an agent that leads to an efficient detection of the carbohydrates. Labeled carbohydrates are also called derivatized carbohydrates. As an example, a fluorescing compound can be used for the labeling of the carbohydrates. Fluorescing compounds are also preferentially charged such that the derivatized compounds can migrate under electrophoretic conditions. When the fluorophore label is uncharged, it can be coupled with a charge imparting species. The fluorophore label also permits the quantitative measurement of the derivatized carbohydrates by fluorescence. Fluorescing compounds such as 9-aminopyrene-1,4,6-trisulfonic acid (APTS) and 8-aminonaphthalene-1,3,6-trisulfonic acid (ANTS) are particularly suitable for electrophoretic separation of derivatized carbohydrates. Other compounds for fluorescent labeling of carbohydrates include 2-aminopyridine(AP), 5-aminonaphthalene-2-sulfonate(ANA), 1-amino-4-napthalene sulfonic acid(ANSA), 1-amino-6,8-disulphonic acid(ANDA), 3-(4-carboxybenzoyl)-2-quinolinecarboxaldehyde(CBQCA), lucifer yellow, 2-aminoacridone and 4-aminobenzonitrile(ABN).

In a particular embodiment, regarding the detection of the fluorescently labeled carbohydrates, any detection method known in the art can be applied, but preferably the detection is carried out with a laser such as a diode laser, a He/Cd laser or an argon-ion laser. In a particular embodiment, the profile of labeled carbohydrate bands produced by the electrophoretic separation is visualized using an imaging system based on a charge-coupled device (CCD) camera. Information from the CCD camera may subsequently be stored in digital form and analyzed by various computer programs for comparing diagnostic carbohydrate patterns between individuals and between reference standards. In another particular embodiment the gel separated diagnostic carbohydrates may be transferred to an immobilizing membrane, i.e., blotted and then probed with various diagnostic carbohydrate-specific reagents such as lectins or monoclonal or polyclonal antibodies specific for diagnostic carbohydrates. In a specific embodiment the invention provides a method to detect liver cirrhosis in a mammal comprising measuring and detecting at least one glycan structure and/or glycoconjugate that has a different abundance in samples derived from individuals with and without cirrhosis by using ligands that specifically bind to at least one glycan structure and/or glycoconjugate. Ligands comprise, for example, lectins and antibodies. For example, the increased abundance of the N-glycan structures (or their conjugates) with a "bisecting GlcNAc" residue (GnT-III product) in a body fluid sample can be detected with a lectin that specifically recognizes glycans (or their conjugates) that are modified with a bisecting GlcNAc, such as the erythro-agglutinating lectin from *Phaseolus vulgaris* (E-PHA). Alternatively, the increased abundance of the N-glycan structures with a "bisecting GlcNAc" residue (or their conjugates) can be detected by a reduction in the binding to the N-glycans (or their conjugates) to lectins that only bind N-glycans (or their conjugates) if they are not substituted with a bisecting GlcNAc residue. An example of such a lectin is the lectin from *Canavalia ensiformis* (Con A). The observed undergalactosylation of the serum glycoprotein N-glycans can be detected by a terminal-GlcNAc binding lectin such as the *Griffonia simplicifolia* II (GS-II) lectin. Alternatively, the undergalactosylation can be measured by a reduction in the binding of a terminal-galactose binding lectin such as the lectin from *Erythrina crystagelli*.

In a particular embodiment, the "profile of a feature determined by the structure of the carbohydrates" is obtained by measuring a property of the carbohydrates, such as whether it is a substrate for a specific glycosyltransferase. In a preferred embodiment, this glycosyltransferase is beta-1,4-galactosyltransferase and the carbohydrates are those present on the total mixture of serum or plasma proteins. An additional substrate for this reaction is UDP-Galactose, and the reaction yields UDP in a stoichiometric amount. Thus, the profile can be obtained by measuring the difference between the extent of galactosylation of the desialylated proteins before and after the reaction, for example by a method involving binding of the glycoproteins to a lectin specific for terminal beta-galactose (such as the lectins known in the art derived from *Ricinus communis* and from *Erythrina crystagalli*, or the galectins such as the one derived from *Coprinus cinereus*). Alternatively, the profile can be obtained by measuring the amount of UDP generated in the beta-1,4-galactosyltransferase reaction on the mixture of serum or plasma proteins, for example by HPLC. The amount of UDP can also be measured using a coupled enzyme reaction with one or more enzymes known from nucleotide metabolism, such as for example a nucleotide diphosphatase such as the yeast Golgi GDPase, which also shows significant hydrolytic activity towards UDP. In this latter case, the profile can be obtained by measuring either UMP or phosphate, using well-known techniques. Still another example of a measurement of UDP involves the use of supramolecular membrane pores with differential affinity for UDP-Gal and UDP, as known in the art. The profiles thus obtained can for example be standardized for the total amount of protein or carbohydrate present in the serum or plasma sample. In yet another embodiment, the profile can be obtained by using the carbohydrates present on the mixture of serum or plasma proteins as substrate for both beta-1,4-galactosyltransferase and a sialyltransferase, with UDP-Galactose and CMP-N-acetylneuraminic acid as sugar donor substrates. In this embodiment, the profile can either consist of the difference in binding of a sialic-acid binding lectin (such as the lectin well known in the art derived from *Maackia amurensis* or *Sambucus nigra*) to the glycoproteins before and after the reaction, or can consist of measuring the amount of UDP and/or CMP released during the reaction, using methods known in the art.

In another embodiment the carbohydrate profiling method can be supplemented pre-electrophoretically with one or more internal standards labeled with a chromophore or fluorophore different from the label attached to the carbohydrate analytes. The internal standard allows for accurate and reproducible determination of the electrophoretic mobilities of the derivatized carbohydrate by referencing these mobilities to the mobilities of the components in the internal standard mixture. For example, a rhodamine-labeled oligonucleotide standard, Genescan™ 500 (Applied Biosystems, Foster City, Calif., USA), or a mixture of rhodamine-labeled 6-, 18-, 30-, and 42-meric oligonucleotides, may be added to the derivatized glycans before profiling. Diagnostics standards may be labeled prior to the labeling of the samples for analysis; however, diagnostic standards are preferably labeled concomitantly with the labeling for the standards for analysis. Furthermore, the diagnostic carbohydrates in the standards are preferably quantitated so as to provide for quantitative or qualitative comparisons with the amount of diagnostic carbohydrates in the samples for analysis.

The term "body fluid" includes, for example, blood, blood serum, blood plasma, saliva, urine, bone marrow fluid, cerebrospinal fluid, synovial fluid, lymphatic fluid, amniotic fluid, nipple aspiration fluid and the like. Preferred body fluids for analysis are those that are conveniently obtained from patients, particularly preferred body fluids include blood serum and blood plasma.

Although the present invention can be carried out without pre-treatment of the sample prior to the profiling of the (derivatized) glycans, in a particular embodiment, samples for analysis may require processing prior to the separation and quantification of the diagnostic carbohydrates. The precise method of sample processing employed may vary in accordance with a number of factors attributable to the choice of sample fluid and the identity of the diagnostic carbohydrates. These factors include, but are not limited to: the abundance of the diagnostic carbohydrate, the concentration of background carbohydrates, the presence of interfering molecules, for example, molecules that adversely affect diagnostic carbohydrate band mobility or the fluorescent labeling of the diagnostic carbohydrates, and whether the fluorescent label has to be separated from the derivatized diagnostic carbohydrates. Suitable methods for processing or pre-treatment of samples include, but are not limited to: dialysis, to remove interfering molecules (e.g., salt for an efficient MS detection); ultrafiltration, to concentrate diagnostic carbohydrates and remove interfering molecules; centrifugation, to remove interfering particulates or concentrate cells; precipitation, to remove interfering molecules; removal of albumin from the serum, to enrich for glycosylated proteins and hence for lower abundance glycans; deglycosylation with a glycosidase (e.g., a sialidase digest of the glycans), to generate a more simple glycan profile; chromatography, such as affinity chromatography, to remove for example albumin from the serum.

In yet another embodiment the invention provides a method to detect liver cirrhosis in a mammal, the method comprising: (a) generating a profile of carbohydrates or fragments derived thereof, or labeled derivatives of carbohydrates or fragments, or features of carbohydrates or carbohydrate fragments that are determined by the structure of carbohydrates or carbohydrate fragments; carbohydrates or fragments being present on or obtained from a mixture of glycoconjugates that are present in or are derived from a sample of a body fluid from a mammal, and (b) measuring the relative amount of at least one carbohydrate or a fragment derived thereof, or a labeled derivative of the carbohydrate or fragment, present in the carbohydrate profile. The term "measuring the relative amount" refers to measuring the relative amounts of at least one carbohydrate or fragment (e.g., one particular carbohydrate or fragment) and differences thereof between two profiles, one profile being derived from a mammal free of liver cirrhosis and another profile derived from a mammal possibly suffering from liver cirrhosis and to be diagnosed for liver cirrhosis. Alternatively, the amount of one particular carbohydrate can be compared between an average reference range taken from mammals free of liver cirrhosis and the measured amount of the particular carbohydrate in a mammal to be diagnosed for liver cirrhosis. In yet another embodiment, the "measuring of the relative amount" refers to measuring the relative amount of at least two carbohydrates or fragments derived thereof or labeled derivatives of carbohydrates or fragments, or features of carbohydrates or carbohydrate fragments present in one carbohydrate profile derived from a sample of a body fluid from a mammal.

In another embodiment of the invention, in order to be able to measure relative amounts of the carbohydrates, diagnostic standards are included on the gels used to analyze the diagnostic carbohydrates in the subject samples; however, the information embodied by the diagnostic standard, for example band migration distance and intensity, may also be obtained from comparison with stored records made from diagnostic standards previously subjected to fluorophore assisted carbohydrate electrophoresis under conditions similar to the conditions to which the samples for analysis are exposed. Diagnostic standards may be both positive, i.e., corresponding to the complete carbohydrate pattern in an afflicted individual, or negative, i.e., corresponding to unafflicted individual. Diagnostic standards may have a composition similar to that of samples for analysis in that they may contain both diagnostic carbohydrates and background carbohydrates with composition similar to that found in actual samples. Diagnostic standards may be derived from samples obtained from afflicted and non-afflicted individuals. Alternatively, diagnostic standards may contain one or more diagnostic carbohydrates free of background carbohydrates.

In a particular embodiment, the diagnostic technique to measure liver cirrhosis does not require an a priori detailed knowledge of the structure of the carbohydrates.

In another particular embodiment, the diagnostic technique measuring liver cirrhosis uses the knowledge of the structure of the carbohydrates. The results of the structural analysis of the differentially regulated glycans can be summarized as an increased abundance of N-acetyl-glucosaminyl-transferase III products (bisecting GlcNAc, glycan structures of peaks 2, 4 and 7 depicted in FIG. 1), a decreased galactosylation of the biantennary glycans (increased intensity of glycan structures of peaks 1 and 2 depicted in FIG. 1), and a decrease in the abundance of the bi- and triantennary fully galactosylated glycan structures (glycan structures of peaks 3 and 8 depicted in FIG. 1).

In another embodiment, the invention provides a method for the detection of liver cirrhosis in a mammal, the method comprising generating a profile of carbohydrates or fragments derived thereof, or labeled derivatives of carbohydrates or fragments, or features of carbohydrates or carbohydrate fragments that are determined by the structure of carbohydrates or carbohydrate fragments; carbohydrates or fragments being present on or obtained from a mixture of glycoconjugates that are present in or are derived from a sample of a body fluid from a mammal, and measuring the amount of at least one carbohydrate or a fragment derived thereof or a labeled derivative of the carbohydrate or fragment, or a feature of at least one carbohydrate or fragment derived thereof present in the carbohydrate profile, wherein at least one carbohydrate is selected from the group consisting of:

(i) GlcNAc(β-1,2)Man(α-1,3)[GlcNAc(β-1,2)Man(α-1,6)]Man(β-1,4)GlcNAc(β-1,4)[Fuc(α-1,6)]GlcNAc(glycan 1), (ii) GlcNAc(β-1,2)Man(α-1,3)[GlcNAc(β-1,4)][GlcNAc(β-1,2)Man(α-1,6)]Man(β-1,4)GlcNAc(β-1,4)[Fuc(α-1,6)]GlcNAc(glycan 2), (iii) Gal(β-1,4)GlcNAc(β-1,2)Man(α-1,3)[Gal(β-1,4)GlcNAc(β-1,2)Man(α-1,6)]Man(β-1,4)GlcNAc (glycan 3), (iv) Gal(β-1,4)GlcNAc(β-1,2)Man(α-1,3)[GlcNAc(β-1,4)][Gal(β-1,4)GlcNAc(β-1,2)Man(α-1,6)]Man(β-1,4)GlcNAc(β-1,4)[Fuc(α-1,6)]GlcNAc(glycan 7), (v) Gal(β-1,4)GlcNAc(β-1,2)[Gal(β-1,4)GlcNAc(β-1,4)]Man(α-1,3)[Gal(β-1,4)GlcNAc(β-1,2)Man(α-1,6)]Man(β-1,4)GlcNAc(β-1,4)GlcNAc(glycan 8), (vi) a fragment derived of glycan 1, 2, 3, 7 or 8, (vii) a sialylated derivative of glycan 1, 2, 3, 7 or 8, and (viii) a feature of glycan 1, 2, 3, 7 or 8 or derivative or fragment thereof.

For the sake of clarity the structures of the peaks 1, 2, 3, 7 and 8 correspond with the carbohydrate profile depicted in FIG. 1 and with the graphic representation of these structures in FIG. 4. The carbohydrate profile is a desialylated profile (without sialic acid on the glycans), meaning that the structures of peaks 1, 2, 3, 7 and 8 are strictly carbohydrate fragments (missing the sialic acid structures). The carbohydrates are herein presented with the IUPAC rules for nomenclature (http://www.chem.qmul.ac.uk/iupac/2carb/38.html), the peaks according to FIG. 1 have been identified in the present invention and are represented by their condensed and extended nomenclature. In the claims, the condensed nomenclature is used. The name of the four structures is summarized here below.

Desialylated glycan structure of peak 1 from FIG. 1:

Condensed nomenclature: GlcNAc(β-1,2)Man(α-1,3)[GlcNAc(β-1,2)Man(α-1,6)]Man(β-1,4)GlcNAc(β-1,4)[Fuc(α-1,6)]GlcNAc.

Extended nomenclature: β-D-GlcpNAc-(1→2)-α-D-Manp-(1→3)-[β-D-GlcpNAc-(1→2)-α-D-Manp-(1→6)]-β-D-Manp-(1→4)-β-D-GlcpNAc-(1→4)-[α-L-Fucp-(1→6)]-D-GlcpNAc.

Desialylated glycan structure of peak 2 from FIG. 1:

Condensed nomenclature: GlcNAc(β-1,2)Man(α-1,3)[GlcNAc(β-1,4)][GlcNAc(β-1,2)Man(α-1,6)]Man(β-1,4)GlcNAc(β-1,4)[Fuc(α-1,6)]GlcNAc.

Extended nomenclature: β-D-GlcpNAc-(1→2)-α-D-Manp-(1→3)-[β-D-GlcpNAc-(1→4)][β-D-GlcpNAc-(1→2)-α-D-Manp-(1→6)]-β-D-Manp-(1→4)-β-D-GlcpNAc-(1→4)-[α-L-Fucp-(1→6)]-D-GlcpNAc.

Desialylated glycan structure of peak 3 from FIG. 1:

Condensed nomenclature: Gal(β-1,4)GlcNAc(β-1,2)Man(α-1,3)[Gal(β-1,4)GlcNAc(β-1,2)Man(α-1,6)]Man(β-1,4)GlcNAc(β-1,4)GlcNAc.

Extended nomenclature: β-D-Galp-(1→4)-β-D-GlcpNAc-(1→2)-α-D-Manp-(1→3)-[β-D-Galp-(1→4)-β-D-GlcpNAc-(1→2)-α-D-Manp-(1→6)]-β-D-Manp-(1→4)-β-D-GlcpNAc-(1→6)-D-GlcpNAc.

Desialylated glycan structure of peak 7 from FIG. 1:

Condensed nomenclature: Gal(β-1,4)GlcNAc(β-1,2)Man(α-1,3)[GlcNAc(β-1,4)][Gal(β-1,4)GlcNAc(β-1,2)Man(α-1,6)]Man(β-1,4)GlcNAc(β-1,4)[Fuc(α-1,6)]GlcNAc.

Extended nomenclature: β-D-Galp-(1→4)-β-D-GlcpNAc-(1→2)-α-D-Manp-(1→3)-[β-D-GlcpNAc-(1→4)][β-D-Galp-(1→4)-β-D-GlcpNAc-(1→2)-α-D-Manp-(1→6)]-β-D-Manp-(1→4)-β-D-GlcpNAc-(1→4)-[α-L-Fucp-(1→6)]-D-GlcpNAc.

Desialylated glycan structure of peak 8 from FIG. 1:

Condensed nomenclature: Gal(β-1,4)GlcNAc(β-1,2)[Gal(β-1,4)GlcNAc(β-1,4)]Man(α-1,3)[Gal(β-1,4)GlcNAc(β-1,2)Man(α-1,6)]Man(β-1,4)GlcNAc(β-1,4

Extended nomenclature: β-D-Galp-(1→4)-β-D-GlcpNAc-(1→2)-[β-D-Galp-(1→4)-β-D-GlcpNAc-(1→4)]-α-D-Manp-(1→3)-[β-D-Galp-(1→4)-β-D-GlcpNAc-(1→2)-≠-D-Manp-(1→6)]-β-D-Manp-(1→4)-β-D-GlcpNAc-(1→4)-D-GlcpNAc.

In another embodiment, the invention provides a method to detect liver cirrhosis comprising the steps of (a) generating a profile of carbohydrates or fragments derived thereof, or labeled derivatives of carbohydrates or fragments, or features of carbohydrates or carbohydrate fragments that are determined by the structure of carbohydrates or carbohydrate fragments; carbohydrates or fragments being present on or obtained from a mixture of glycoconjugates that are present in or are derived from a sample of a body fluid from a mammal and (b) measuring the relative amount of the glycan structure 1, or a fragment thereof, and the glycan of structure 8, or a fragment thereof; and/or the glycan of structure 2, or a fragment thereof, and the glycan of structure 8, or a fragment thereof; and/or the glycan of structure 7, or a fragment thereof, and the glycan of structure 8, or a fragment thereof; and/or the glycan of structure 1, or a fragment thereof, and the glycan of structure 3, or a fragment thereof; and/or glycan of structure 2, or a fragment thereof, and the glycan of structure 3, or a fragment thereof; and/or the glycan of structure 7, or a fragment thereof, and the glycan of structure 3, or a fragment thereof.

The average peak heights for glycan structures 1, 2, 7 and 8 were calculated in the different patient groups. The average relative amounts between these glycan structures for the cirrhosis group (n=37) are: peak 1/peak 8: 2.444, peak 2/peak 8: 0.590 and peak 7/peak 8: 1.479. Relative amounts for the healthy control group (n=60) are: peak 1/peak 8: 0.809, peak 2/peak 8: 0.081, and peak 7/peak 8: 0.7234. This means that a sample is diagnosed as having cirrhosis when the relative amount of peak 1/peak 8 is 3.02 times higher than the average within this healthy population, and/or when the relative amount of peak 2/peak 8 is 7.28 times higher than the average within this healthy population, and/or when the relative amount of peak 7/peak 8 is 2.04 times higher than the average within this healthy population.

Relative amount of these glycan structures for the chronic hepatitis group (n=27) are: peak 1/peak 8: 1.21, peak 2/peak 8: 0.25 and peak 7/peak 8: 0.95. This means that a sample is diagnosed as having cirrhosis when the relative amount of peak 1/peak 8 is 2.01 times higher than the average within this chronic hepatitis group and/or when the relative amount of peak 2/peak 8 is 2.36 times higher than the average within this chronic hepatitis group, and/or when the relative amount of peak 7/peak 8 is 1.56 times higher than the average within this chronic hepatitis group.

Relative amounts between these glycan structures for the complete control population (n=153, consisting of healthy individuals, individuals suffering from chronic hepatitis and individuals suffering from chronic alcoholism) are: peak 1/peak 8: 0.98, peak 2/peak 8: 0.115 and peak 7/peak 8: 0.87. This means that a sample is diagnosed as having cirrhosis when the relative amount of peak 1/peak 8 is 2.49 times higher than the average within this complete control population, and/or when the relative amount of peak 2/peak 8 is 5.13 times higher than the average within this complete control population, and/or when the relative amount of peak 7/peak 8 is 1.7 times higher than the average within this complete control population.

Thus, in another embodiment, when the ratio (relative amounts) of peak 1/peak 8 is higher than at least 20%, at least 30%, at least 40%, at least 50%, at least 60%, at least 70% or at least 80% of the relative amount of the average within the control population, a sample is diagnosed as being derived from a mammal suffering from liver cirrhosis.

In a specific embodiment, the invention provides a method to detect liver cirrhosis comprising the steps of: (a) generating a profile of carbohydrates or fragments derived thereof, or labeled derivatives of carbohydrates or fragments, or features of carbohydrates or carbohydrate fragments that are determined by the structure of carbohydrates or carbohydrate fragments; carbohydrates or fragments being present on or obtained from a mixture of glycoconjugates that are present in or are derived from a sample of a body fluid from a mammal, and (b) measuring the relative amount of the glycan of structure 1, or a fragment thereof, and the glycan of structure 8 and wherein the relative amounts of glycan structures or fragments thereof is at least 80% higher than the average of the relative amount in mammals free of liver cirrhosis.

In another embodiment, when the relative amount of peak 2/peak 8 is higher than at least 20%, at least 30%, at least 40%, at least 50%, at least 60%, at least 70%, at least 80%, at least 90% or at least 100% of the relative amount of the average within the control population, a sample is diagnosed as being derived from a mammal suffering from liver cirrhosis.

In a specific embodiment, the invention provides a method to detect liver cirrhosis comprising the steps of: (a) generating a profile of carbohydrates or fragments derived thereof, or labeled derivatives of carbohydrates or fragments, or features of carbohydrates or carbohydrate fragments that are determined by the structure of carbohydrates or carbohydrate fragments; the carbohydrates or fragments being present on or obtained from a mixture of glycoconjugates that are present in or are derived from a sample of a body fluid from a mammal, and (b) measuring the relative amount of the glycan of structure 2, or a fragment thereof, and the glycan of structure 8 and wherein the relative amount between glycan structures or fragments thereof is at least 100% higher than the average of the relative amount in mammals free of liver cirrhosis.

In yet another embodiment when the relative amount of peak 7/peak 8 is higher than at least 20%, at least 30% or at least 40% of the relative amount of the average within the control population, a sample is diagnosed as being derived from a mammal suffering from liver cirrhosis.

In another specific embodiment, the invention provides a method to detect liver cirrhosis comprising the steps of (a) generating a profile of carbohydrates or fragments derived thereof, or labeled derivatives of carbohydrates or fragments, or features of carbohydrates or carbohydrate fragments that are determined by the structure of carbohydrates or carbohydrate fragments; carbohydrates or fragments being present on or obtained from a mixture of glycoconjugates that are present in or are derived from a sample of a body fluid from a mammal, and (b) measuring the relative amount of the glycan structure 7 or a fragment thereof and the glycan structure 8 and wherein the relative amount between glycan structures or fragments thereof is at least 40% higher than the average of the relative amount in mammals free of liver cirrhosis.

In another embodiment, the invention also includes a kit for performing diagnosis of liver cirrhosis. For example a kit can be made for performing fluorophore assisted carbohydrate electrophoresis diagnosis of liver cirrhosis. As another non-limiting example, a kit can be made for performing MS diagnosis of liver cirrhosis. Fluorophore assisted carbohydrate electrophoresis diagnosis kits provide collections of reagents required for performing the diagnosis of liver cirrhosis. Suitable kits enable laboratories to conveniently perform fluorophore assisted carbohydrate electrophoresis diagnosis. Kits may include, for example, reagents for performing tests to identify liver cirrhosis. Kits may include, for example, diagnostic standards, fluorescent label, blotting and binding materials, for example, membranes, carbohydrate specific binding reagents, lectins, instructions, sample containers, and polyacrylamide gel reagents, precast gels, enzyme buffers, reducing agents (for use in the fluorophore labelling of carbohydrates), and glycosidase enzymes (e.g., sialidase, galactosidase, fucosidase) capable of catalyzing reactions that structurally alter diagnostic carbohydrates. More complete kits may include, for example, equipment for performing fluorophore assisted carbohydrate electrophoresis, such as polyacrylamide gel apparatus, CCDs, laser, DNA sequencer, computers, software, and the like. Reagents included in fluorophore assisted carbohydrate electrophoresis diagnosis kits are preferably provided in pre-measured amounts. The kits preferably include the instructions for carrying out the fluorophore assisted carbohydrate electrophoresis method of the present invention.

The diagnostic test is useful in practice because it is sufficiently easy to apply on a large scale by normally trained laboratory staff. Furthermore, since electrophoresis-based high-resolution and high-sensitivity analyzers for DNA sequencing and mutation detection are already present in a rapidly increasing number of clinical laboratories or are affordable for most clinical laboratories, the novel diagnostic glycomics test for liver cirrhosis can be run on them. Moreover, the available range of DNA-analyzers allows for the sample throughput to be easily scaled from just a few to hundreds of samples per day per machine, depending on the demand of each laboratory. This DNA-analysis equipment offers the added advantage of automation, reducing the complexity of the overall analytical process. The profiling on the total mixture of glycoproteins increases the tolerance of the test for small inter-individual variations of the abundance and the glycosylation pattern of each individual glycoprotein in the mixture and thus allows more robust testing than the current classical approaches where the glycosylation is studied on purified glycoproteins.

In another embodiment, the method for the detection of liver cirrhosis further comprises clinical chemistry parameters and/or histological data. Thus, the present invention can also be conveniently carried out in combination with clinical chemistry parameters and/or histology and/or imaging parameters. Measurement of clinical chemistry parameters comprises measurement of levels of bilirubin, albumin, prothrombin time, C-reactive protein, IgA abundance, serum hyaluronic acid concentration, aminotransferases and several liver metabolism test known in the art. Histology comprises liver biopsies. Imaging comprises ultrasound, CT-scan, MRI-scan and imaging of radioactive tracers specific for the liver.

In yet another embodiment, the invention provides a method to detect the presence or the predisposition of hepatocellular carcinoma in a mammal suffering from liver cirrhosis, comprising: (a) generating a profile of carbohydrates or fragments derived thereof, or labeled derivatives of carbohydrates or fragments, or features of carbohydrates or carbohydrate fragments that are determined by the structure of carbohydrates or carbohydrate fragments; carbohydrates or fragments being present on or obtained from a mixture of glycoconjugates that are present in or are isolated from a sample of a body fluid from a mammal, and (b) measuring in the profile of step (a) the amount of at least one carbohydrate or a fragment derived thereof or a labeled derivative of the carbohydrate or fragment, or a feature of at least one carbohydrate or fragment derived thereof present in the carbohydrate profile, and (c) comparing the measured data obtained in step (b) with measured data obtained from profiles derived from mammals suffering from liver cirrhosis but free of hepatocellular carcinoma, and (d) attributing the deviation obtained in step c) to the presence of hepatocellular carcinoma. In yet another embodiment, in the method to detect the presence or the predisposition of hepatocellular carcinoma in step (c), a two-parameter analysis is carried out with glycans 7 and 14 derived from a human serum carbohydrate profile. In yet another embodiment the two-parameter analysis is a two-parameter binary logistic regression analysis.

The examples which follow are offered as descriptive of certain embodiments. As such they are exemplary only and are not limiting in their nature.

EXAMPLES

Data Collection and Glycomic Serum Profile Characteristics

Profiles of the N-glycan pool present on the complete collection of proteins present in the 214 human sera were obtained, starting from 5 µl serum, without any pre-treatment.

The Applied Biosystems 377 DNA-sequencer was used for this study. The peak height of 14 peaks was quantified in every analyzed serum sample, accounting for >99% of the total observed signal intensity. We limit the discussion here to the nine peaks in the mobility range of 8 to 12 glucose units (FIG. 1). Their intensity is sufficiently high to allow easy routine quantitation.

Statistical Processing

Staying true to the "omics" setup of our study, we approached data analysis in a purely statistical way, without bias towards the identity of the measured peaks.

In FIG. 2, an overview is given of the data characteristics (median and interquartile ranges) for these nine peaks over seven sample groups. Early in the analysis, we observed that a very similar profile change occurred in samples from patients suffering from hepatocellular carcinoma and from patients with liver cirrhosis (the general characteristics of this profile change are evident from comparison of the two lower panels in FIG. 1). Since all of the patients with hepatocellular carcinoma in this study also had liver cirrhosis (16), we decided to regard these samples as one group (n=37, group 1 in Table I) in the further statistical analysis, designated as the cirrhosis group. Group 0 consists of the 60 control samples from Red Cross blood donors. All samples from patients with chronic hepatitis B or C, without cirrhosis, were taken together in group 2 (n=27). Group 3 consists of eight samples from patients with non-HCC metastases to the liver. In group 4, all samples were assembled from patients with suspected chronic alcohol abuse and a positive carbohydrate deficient transferrin (CDT) test result. The glycosylation degree of serum transferrin is responsive to recent (2-3 weeks) alcohol intake and is currently the best serum marker for the detection of chronic alcohol abuse (Anton, 2001; Wuyts et al., 2001). The presence of CDT may influence the glycosylation profile of total serum glycoprotein measured herein. For comparison purposes, group 5 consists of samples (n=33) of chronic alcohol abusers with a negative CDT. Group 6, finally, consists of samples from patients with auto-immune disorders (n=24). Glycosylation changes (especially undergalactosylation and increased presence of α-1,6-linked core fucose) of IgG have been well documented in rheumatoid arthritis and ankylosing spondylitis (Martin et al., 2001; Watson et al., 1999) and could also influence the glycan pattern of total serum glycoprotein, as IgG is a very abundant serum protein.

From the data in FIG. 2, it is apparent that in the cirrhosis group, peaks 1, 2 and 7, are up-regulated, and peaks 3 and 8 are down-regulated, sufficiently so that the inner interquartile range of their values for the cirrhosis group do not overlap with the inner interquartile ranges of the control group (Group 0). Moreover, these changes are highly correlated, as shown by Spearman correlation analysis (Table 2). Therefore, we created new variables by scaling the up-regulated peaks 1, 2 and 7 to the down-regulated peak 8, and subsequently log-transformed these new variables to normalize the distributions. An analysis that took the differential amount of Peak 4 into account did not improve the classification efficiency (see below), and neither did incorporation of the down-regulation of Peak 3. The values for the resulting three new variables are summarized in the right panel of FIG. 2. To detect significant differences in the means of the values for these variables between the seven sample groups, one-way analysis of variance was performed, followed by two different multiple comparison tests (Tukey's Honestly Significant Difference test and Scheffe's comparison) to pinpoint the specific intergroup differences. At a family-wise error rate of 0.0001, for all three variables, the Cirrhosis group was significantly different from all other sample groups (Table 3). The classification efficiency of this difference was evaluated with non-parametric Receiver Operating Curve (ROC) analysis and with binary logistic regression. For optimal clinical relevance and after consultation with the collaborating hepatologist (Dr. H. Van Vlierberghe, UZGent), these classification algorithms were used in a comparison of the Cirrhosis group and the group of patients with chronic hepatitis B or C. In a typical gastro-enterology clinical setting, the detection of cirrhosis is the most relevant in patients with chronic hepatitis (and in patients with chronic alcohol abuse). The group of samples from patients with chronic alcohol abuse that was at our disposition was insufficiently well characterized as to the presence of cirrhosis to include this collection in this cut-off value determination. The results of the ROC analysis are shown in FIG. 3.1, and allow very satisfactory classification efficiencies of around 95%. The cut-off values obtained from these ROC curves (value at which highest combined sensitivity and specificity is attained) are represented as the lines dividing the two-dimensional scatterplots in the rest of FIG. 3 in quadrants. The skewed line dividing the scatterplots in two halves are the regression lines calculated from a linear binary logistic regression model for each two variables. It is instructive to compare the efficiency of the calculated cut-off values and regression lines in the distinction between the Cirrhosis group and all the other sample groups (FIGS. 3.2-6). It is a general observation that the "double ROC" classification has a higher specificity and a lower sensitivity than the regression approach. In the distinction of the Cirrhosis group and the chronic hepatitis group, sensitivity and specificity are both in the range of 90-98%. As can be seen in FIG. 3.3, the sample group of healthy Red Cross blood donors has no (for left and right plot) or only one (on 60, for the center plot) false positives for the double ROC classification and no (for right plot) or one (center and left) false positives for the regression approach. This close to 100% specificity at around 95% sensitivity is very similar to the values obtained in the distinction with chronic hepatitis and indicates again that the measured variables indicate a pathological change that is specific for cirrhosis and does not change significantly with the onset of chronic hepatitis (as can also be derived from ANOVA results). A particular observation is that there are more false positives in the sample group from chronic alcoholics (FIG. 3.4) in regression analyses that incorporate the parameter Log (Peak 7/Peak 8). However, double ROC classification with one of the other two parameters still keeps these cases out of the "positive area." In the group of auto-immune diseases (FIG. 3.5), the false positives were mainly due to increased values of Log (Peak 1/Peak 8) in 25% of the cases and due to increased values of Log (Peak 7/Peak 8) in 17% of the cases. Log (Peak 2/Peak 8) was only trespassing the cut-off value in 1 case (4%). Again, double ROC analysis was more successful than binary logistic regression in keeping these cases out of the positive area. FIG. 3.6 gives a total picture of all of these analyses. Overall, the combination of the parameters in the leftmost plot yields the best result for this assembly of "samples of convenience," with a sensitivity and specificity of 95% via binary logistic regression and a sensitivity of 92% and specificity of 98% via double ROC analysis.

Structural Analysis of the Differentially Regulated N-Glycans

The results as presented in the last paragraph have value in their own for the differentiation of patients with cirrhosis from patients with less far advanced chronic liver disorder. However, to increase confidence in the information obtained from an "omics" approach to a biological problem, an attempt is usually made to relate the outcome of the statistical data processing to already known aspects of the problem under study. For glycomics, a prerequisite to be able to evaluate such a relation is the structural analysis of the glycans that are differentially "expressed." By making use of exoglycosidase arrays, it was possible for us to obtain sufficient structural information on the differentially regulated glycans. Several additional elements made this possible: first, the N-glycans present in "healthy" human serum have been reportedly mapped in a three-dimensional HPLC approach (Nakagawa et al., 1995). This study constitutes a true "catalogue" of the N-glycans that are present on the glycoproteins in normal serum, and thus is a resource that, for our study, is comparable in value as a fully annotated proteome in a proteomics study. Second, from our diagnostic studies, samples were available with a broad quantitative range in the changes of interest. This was very helpful in "tracing" the peaks of interest through the post-exoglycosidase array profiles. The exoglycosidase sequencing of three of these samples is shown in FIG. 4. The structure of five of the major peaks in the profile of healthy serum (structures and their exoglycosidase products) are shown as black peaks in FIG. 4. The position of reference glycans with these structures, and some of their exoglycosidase products, are shown in the bottom panel of the middle sequence. This panel was assembled from individual panels, each containing one of these peaks. The availability of these structures considerably simplified the task of tracing the remaining, differentially regulated peaks through the profiles.

Glycan Structure Corresponding with Peak 1 in FIG. 1

Peak 1 shifts 1.2 glucose units upon fucosidase digestion, to the position of the α-galacto biantennary reference glycan (first peak in the reference panel at the bottom of the central sequencing column). Moreover, upon galactosidase digestion, the peak at this position becomes very intense because Peak 6 shifts to this position (structure of Peak 6: bigalacto core-fucosylated biantennary glycan. Taken together, these data demonstrate that Peak 1 is the biantennary, α-galacto, core-α-1,6-fucosylated glycan. Its up-regulation in the Cirrhosis sample group thus signals a combination of under-galactosylation and increased core fucosylation of the serum glycoproteins.

Glycan Structure Corresponding with Peak 2 in FIG. 1

The identification of this peak is more difficult due to its relatively low abundance. Nevertheless, sufficient information can be derived to positively identify its structure. In the profile resulting from double digestion with sialidase and β-1,4-galactosidase, the product of peak 7 exactly co-migrates with peak 2 in the sialidase panel. Subsequently, as peak 2 is not observed in the left sequencing column (hepatitis sample), we can identify its exoglycosidase products in the sialidase+fucosidase double digestion pattern of the other two samples, where peak 2 is detectable. No peak is present anymore at the position of Peak 2 upon fucosidase digestion, and there is only one new peak that can be the digestion product (highlighted in gray, first arrow in the sialidase+fucosidase profile of the middle sequencing column). In the triple digestion profile (supplementary β-1,4-galactosidase), this peak becomes more intense because the digestion product of Peak 7 comigrates with it. Supplementary digestion with hexosaminidase leaves no trace of a peak at this position. This leads us to the conclusion that Peak 2 represents the bisected, agalacto core-α1,6-fucosylated structure. Thus, this peak bears a combination of the structural alterations of peak 3 and peak 7, i.e. it is non-galactosylated and it has a bisecting GlcNAc residue.

Glycan Structure Corresponding with Peak 3 in FIG. 1

This is the most abundant N-glycan on total serum glycoproteins. After sialidase digestion, its size is estimated to be nine monosaccharide units by comparison to the malto-oligosaccharide reference ladder. After sialidase/β-1,4-galactosidase digestion, this glycan loses two galactose residues and it further loses two GlcNAc residues upon digestion with β-N-acetylhexosaminidase. The residual glycan migrates at the position of the Man$_3$GlcNAc$_2$ core N-glycan structure. We conclude that the structure of glycan nr.3 is biantennary, bi-β-1,4-galactosylated. This conclusion is corroborated by its exact comigration with a reference glycan of this structure, both undigested and digested with β-1,4-galactosidase. Peak 3 is down-regulated in cirrhosis with the increased abundance of its undergalactosylated product (or precursor) and the increased presence of other biantennary glycans, for which this basis biantennary substrate is the precursor.

Glycan Structure Corresponding with Peak 7 in FIG. 1

This peak is also present at relatively low abundance in the profile of serum from a patient with chronic hepatitis (third arrow in second panel of the left sequencing column in FIG. 4) and in normal serum (not shown). Its sequencing can most easily be followed in the third sequencing column, representing one of the most severely affected sera in our collection. Peak 7 is the third most abundant glycan in this profile and this peak, nor any of its digestion products co-migrate with one of the reference glycans mentioned above or their digestion products. As no comigration is seen down to the quadruple exoglycosidase digest, this most likely means that a substituent is present that is absent from these reference glycans. After the quadruple digest, the Peak 7 digestion product migrates 1 glucose unit slower than the trimannose core oligosaccharide, which means that a substituent is present on this trimannose core with a size of one monosaccharide. From the mapping study of total serum glycoprotein N-glycans, this can only be a so-called bisecting GlcNAc. That this substituent is resistant to digestion in these conditions with Jack Bean β-N-acetylhexosamimidase is not unexpected, as bisecting GlcNAc residues are known to be particularly resistant to enzymatic removal (confirmed by the resistance of this residue on a reference glycan to the same exoglycosidase treatment as used here, see FIG. 4, reference panel under the third sequencing column). Fucosidase digest induces a shift of 1.2 glucose units, which signals the presence of a core-α-1,6-linked fucose residue. Supplementary β-1,4-galactosidase digestion shifts the peak another 2 glucose units, which indicates the presence of two β-1,4-galactose residues. Thus, we conclude that Peak 7 represents the bisected biantennary, bi-β-1,4-galactosylated, core-α-1,6-fucosylated glycan structure. This result is corroborated by the co-elution of all of Peak 7's digestion products with the corresponding digestion products of a reference glycan with this structure (bottom panel of the right sequencing column, the panel was assembled from the electropherograms of different lanes, each containing the digestion products of one specific exoglycosidase array on the reference glycan with structure 7). This bisecting GlcNAc substituent is the product of N-acetyl-glucosaminyl-transferase III (GnTIII) activity on the structure represented by Peak 6, the core-α-1,6-fucosylated variant of Peak 3.

Glycan Structure Corresponding with Peak 8 in FIG. 1

The glycan corresponding to peak 8 is about two monosaccharide units longer than glycan 3, is not digestable by bovine kidney fucosidase and comigrates with a triantennary fully β-1,4-galactosylated reference glycan. Moreover, β-1,4-galactosidase removes three galactose residues from the glycan, after which the glycan is one monosaccharide unit longer than the remnant of glycan 3, in accordance with the one extra GlcNAc residue that is expected for a triantennary glycan when compared to a biantennary structure. In conclusion, peak 8 represents a 2,4-branched triantennary, tri-α-1,4-galactosylated glycan structure.

Glycan Structure Corresponding with Peak 9 in FIG. 1

This glycan is one glucose unit longer than the triantennary unfucosylated glycan of peak 8 and is sensitive to both bovine kidney and almond meal fucosidase. After these digestions, the glycan is converted to peak 8. Thus, the fucose residue present on this glycan is α1,3/4 linked. We conclude that the glycan of peak 9 is a branch-fucosylated derivative of glycan 8. The exact position of the branch fucose residue cannot be determined using exoglycosidase digestions.

Glycans Corresponding with other Peaks in FIG. 1

Peak 4 is also up-regulated in the Cirrhosis group, albeit not sufficiently for the inner interquartile range not to overlap with the one of the control group. Its full structure is difficult to elucidate unambiguously using only exoglycosidases since its position in the sialidase-digested profile overlaps with one of the core-fucosylated monogalactosylated biantennary glycans. This monogalactosylated glycan is responsible for most of the Peak 4 intensity in the sialidase-digested profile of normal serum. That it is not this structure which is present in increased amounts in the sera of Cirrhosis patients is suggested by the following observation: upon supplementary β-1,4-galactosidase digestion, a peak appears at the same position as described above upon fucosidase digestion of Peak 2. This indicates that a galactosylated variant of Peak 2 must be present in the diseased sialidase-treated profiles, which is one or two galactose residues larger. The only differentially regulated peak that fulfils these requirements and has not been identified up to here is Peak 4. The distance between Peak 4 and its β-1,4-galactosidase product is exactly the same as between the biantennary, bigalactosylated glycan and its β-1,4-galactosidase product, which is strong evidence for the presence of two β-1,4-linked galactose residues on Peak 4. Thus, we tentatively assign at least part of the increased peak intensity of Peak 4 in Cirrhosis to the bisected, bigalactosylated glycan (without fucosylation).

MS assays will be necessary to positively identify the other peaks, many of which are most probably monogalactosylated variants of the structures described above.

Analysis of the Core-α-1,6-Fucosylation.

An increased expression of the α-1,6-fucosyltransferase has been reported (Noda et al., 1998) in hepatocellular carcinoma. As several of the up-regulated peaks (1, 2 and 7) and the not differentially regulated Peak 6 identified in the preceding paragraph bear an α-1,6-linked fucose residue on the proximal GlcNAc of the N-glycan core, it was of interest to investigate the characteristics of a variable composed of these four peak heights. Therefore, the peak heights of these four peaks were added and one-way ANOVA was performed over the same groups as described above for the other variables, followed by the same multiple comparison tests at the 0.0001 family-wise error rate. The results are presented in FIG. 5. The mean of the group with Cirrhosis was significantly different from the mean of all other groups. When the Cirrhosis group was split in cases with and without HCC, no significant difference in the degree of core fucosylation could be detected (t-test, P>0.1).

Development of a Clinically Useful High-Throughput Deglycosylation and Labeling Protocol Using only a PCR Thermocycler The available deglycosylation and labeling protocols are still relatively labour-intensive and from serum to desialylated labeled glycans ready for analysis, they take about two and a half days. The complete analysis can be performed in three standard working days. In a basic research environment, the protocols are largely satisfactory, but would be more cumbersome in a clinical research laboratory because some pieces of equipment are not in general use (plate and vacuum centrifuges). Even more importantly, the currently available protocols involve several tube-to-tube transfers and manual procedures that are difficult to validate as sample tracking becomes relatively complicated. Also, the labor involved and the quite lengthy time from sample to results are not favorable for easy implementation in the clinical lab. Therefore, we decided to radically rethink the sample preparation procedure, from a truly applied viewpoint. As the serum glycoprotein concentration is very high (almost all proteins except for albumin are glycosylated, which means about 35 g glycoprotein per liter), a 5 µl sample contains about 175 µg glycoprotein.

Further calculating with an estimated average MW for the serum glycoproteins of 50 kDa and three occupied N-glycosylation site per molecule, a rough estimate of 10 nmol N-glycan in this 5 µl serum sample is obtained. Knowing that a peak of 15 fmol is easily detected on DSA-FACE and that, to have a relatively complete profile, one should be able to detect peaks representing about 0.5% of the total glycan pool, about 5 pmol labeled glycan is desirable at the analysis stage of the protocol. This means that there is a broad 3000-fold margin between the amount of N-glycans that we have available and the amount we actually need for the analysis. This broad margin can be sacrificed to making some steps in the sample preparation protocol less efficient, but easier to apply.

Looking for an affordable and familiar apparatus that is designed to handle small-volume fluid samples with minimal evaporation, we found that the thermocyclers with heated lid used for PCR seemed suitable for this. Then, by careful consideration of the subsequent buffer systems used, a procedure was developed that only involves fluid addition/removal and dilution, from serum to ready-to-analyse labeled N-glycans.

Protocol for PCR-Machine Based Serum Protein N-Glycan Labeling:

1) Add 5 microliters serum to a PCR tube (or a tube of a 96-well PCR plate) and add 1 microliter of a 10% SDS-containing 20 mM NH$_4$Ac buffer, pH 7. Mix and close the tube. Put in a thermocycler with heated lid and heat at 96° C. for 5 min. Make the thermocycler cool down (this step denatures the glycoproteins to increase accessibility for PNGase F).

2) Add 1 microliter 10% NP-40 solution to neutralize the SDS-denaturing effect on PNGase F (standard procedure for PNGase F digest). Add 2 microliters PNGase F solution (1000 Biolabs units). Close the tube and heat in the thermocycler at 37° C. for three hours.

3) Transfer 1 microliter of the solution to another PCR tube (or 96-well PCR plate) and keep this sample separated from the others during the desialylation (step 4). This sample will give the profile of the sialylated glycans, if required.

4) Add 8 microliters 50 mM NaAc buffer pH 5 and mix. (This amount of buffer was calculated to take into account the bicarbonate-based buffering capacity of serum and is enough to compensate for two-fold variations in this buffering capacity, which is much more than ever observed clinically). Add 2 µU (2 microliters) *Arthrobacter ureafaciens* sialidase. Close the tube and heat in the thermocycler at 37° C. for 3 hours.

Take 1 microliter and transfer to a new PCR tube (or plate). Alternatively (but less accurately due to minimal evaporation effects), remove 19 microliters from the tube and process the remaining 1 µl. Also take the tubes from step 3 (sialylated glycans) and process both samples similarly through the remainder of the protocol.

6) On the thermocycler, insert the tubes with lids open and the lid of the cycler open and heat to 65° C. This evaporates the samples, which is complete in less than five minutes due to the very small volumes (1 µl).

7) Prepare the labeling solution containing 10 mM APTS in 0.6 M citric acid and 0.5 M sodium cyanoborohydride in 50% DMSO. Add 1.5 microliters of this labeling solution to the bottom of the now dry PCR tubes. Close the tubes very well and with the heated lid on, heat at 90° C. for one hour. This is the fast-kinetics labeling chemistry for desialylated glycans. For the sialylated glycans, the labeling solution is the same but the temperature should be kept at 37° C. and the reaction should be done overnight, to avoid desialylation.

8) Add 150 microliters water to every tube to stop the reaction and dilute the label to about 100 pmol/µl. The resulting solution can be directly used for loading on DNA sequencers (after addition of formamide and internal standard). In early experiments, we determined that 100 pmol free label represents the maximum tolerable amount that can be loaded on a sequencing gel lane without extensively overloading the separation capacity of the gel.

Overall, this protocol leads to the presence of 1/3000th of the original amount of N-glycans in 1 µl of the labeled glycan preparation.

Four serum samples of healthy donors were analyzed as described above. The signal intensity and data quality are very satisfactory, proving the principle that serum N-glycan sample preparation can be achieved using only a relatively cheap thermocycler, with very little tube transfers. This method provides for the potential for (semi)-automation, analogous to large-scale PCR setup. Implementation of this protocol allows serum analysis for cirrhosis to be completed with a turn-around time of 24 hours (or less if faster analyzers based on capillary arrays can be used). We are convinced that this improvement in the sample preparation procedure brings the diagnostic test for liver cirrhosis much closer to actual use in routine clinical chemistry.

Validation of the Diagnosis of Liver Cirrhosis in an Independent Patient Group

To validate the cut-off values for cirrhosis detection obtained in the above study, an independent group of chronic hepatitis patients with (n=10) or without (n=13) cirrhosis was classified using these cut-off values. As can be seen in FIG. 3, section 8, a classification efficiency of 91% was obtained for all three parameter combinations. Thus, although the size of this second subject group is rather small, we conclude that the classification model derived from our optimization group is not over-fitted and that the >90% classification efficiency is conserved.

Comparison Between Classical Clinical Chemistry Parameters and Glycoprofiling for Liver Cirrhosis Detection In the present invention the efficiency of the derived parameters to discriminate between HCC and/or cirrhosis and non-cirrhotic chronic hepatitis B and C was evaluated with Receiver Operating Curve (ROC) analysis. The results of the ROC analysis indicate classification efficiencies of around 95%. ROC analysis in the same sample group of only classical clinical chemistry parameters related to liver dysfunction (FIG. 3, section 7) yields values of: 76±6% for total bilirubin and 80±5% for serum albumine, whereas AST, ALT, GGT and CRP yielded non-significant AUC values: P>0.05. In addition, for the subgroup of 14 "compensated" cirrhosis cases (cirrhosis cases with normal bilirubin and albumin levels) in our cirrhosis study group with serum, total bilirubin and serum albumin concentrations within the reference range (total bilirubin <1.3 mg/dL and serum albumin >3.5 g/dL), we assessed how many of these fell within the positive region for each of the three markers derived from the glycan profile of total serum proteins (cut-offs determined by ROC analysis of the markers in the distinction between chronic hepatitis without cirrhosis and the total cirrhosis group (both compensated and decompensated for albumin and bilirubin). For log(Peak 1/Peak 8), this was 12/14 (85.7%); for log(Peak 2/Peak 8): 11/14 (78.5%); for log(Peak 7/Peak 8): 11/14 (78.5%). On average, these markers can detect about 80% of cirrhosis cases that were missed by both serum albumin and serum total bilirubin measurement. This clearly demonstrates that the glycomarkers of this invention perform better than the currently available standard clinical chemistry markers used in the routine assessment of chronic liver patients. Thus, our glycoprofiling markers detect liver cirrhosis in an earlier stage of the disease.

Diagnosis of Hepatocellular Carcinoma (HCC) in Patients Suffering from Liver Cirrhosis As disclosed so far, all cases with HCC were taken together with the cirrhosis group, as all but one of them had underlying cirrhosis. However, it is known in the art that the current diagnosis of HCC on a cirrhosis background is difficult and there is significant room for improvement. Therefore, within the HCC and/or cirrhosis group described above, we screened for alterations in the serum N-glycome pattern that could pinpoint the HCC cases. ROC analysis of all 14 detected peaks (see FIG. 1) within the HCC and/or cirrhosis group indicated that the abundance of Peaks 5, 7 and 14 had significant differentiating power (ROC; P<0.05). We found that a two-parameter analysis with Peak 7 and 14 had the best classification efficiency (FIG. 6). This was assessed with a two-parameter binary logistic regression model, the regression line of which is shown in FIG. 6 (a case falling on this line would have equal probability to fall in either of the two differentiated categories). The logistic function of this model was: Z=−0.649[% Peak 7]+5.722[% Peak 14]+2.967. Classification based on this model detected HCC cases with a sensitivity of 71% and a specificity of 91% (overall classification efficiency: 82%). The structure of Peak 14 could not be assigned due to its low abundance. Further MS characterization is ongoing. We speculate that this glycan is a product of N-acetyl-glucosaminyl-transferase V, as it runs in a position compatible with a tetra-antennary glycan and as increased GnT-V activity is a hallmark of many tumors.

Materials and Methods

Study Design

The clinical study was based on convenient samples and was approved by the local ethical committee of the University Hospital Ghent. A sample of 73 patients (presenting with symptoms of chronic liver disorders) at the Gastroenterology Department of the University Hospital Ghent over a one-year period (12/2000-12/2001) were included in the study. The diagnosis of chronic hepatitis B (n=8) and C (n=39) was made by a raised ALT level (above the upper limit of normal) in at least two blood samples in a time period of six months in the presence of either detectable hepBsAg and HBV DNA, or detectable anti-HCV antibodies and HCV RNA. In the patients with no contra-indications for a liver biopsy (clotting disorders, presence of ascites, . . . ), this was confirmed by a percutaneous liver biopsy. The diagnosis of cirrhosis (n=37) was made on clinical (presence of ascites, varices, encephalopathy) and biochemical grounds (albumin and bilirubin level, INR) in the patients with a decompensated cirrhosis. In the other patients (when contra-indications for a liver biopsy were absent), diagnosis was made by a percutaneous liver biopsy. The underlying etiology of the cirrhosis was chronic alcohol abuse (n=15) and chronic hepatitis (n=20). In one case each, the etiology of the cirrhosis was auto-immune hepatitis or unknown (cryptogenic cirrhosis). In the patients with cirrhosis, the diagnosis of a hepatocellular carcinoma (HCC, n=16) was made by the presence of a rise in alfa-fetoprotein or the presence of a focal liver lesion on ultrasound, CT or MRI with the characteristics of a HCC; in some of the patients, both were present. In the absence of cirrhosis and in patients where there was doubt about the diagnosis, a true cut needle biopsy of the focal lesion was performed. The clinical center where the diagnosis was performed is the reference center for HCC for Flanders, a low-incidence region for HCC of about 6 million inhabitants, mainly Caucasian but with important Italian, Turkish and Morrocan communities (about 15% of the population).

Also, a sample was included of 58 patients with suspected chronic alcohol abuse and admitted for this reason to the Department of Psychiatry, Academic Hospital Stuivenberg in Antwerp (a major city in the Flanders region). Recent heavy alcohol consumption was evaluated by the Carbohydrate Deficient Transferrin measurement (% CDT-TIA™, Axis Biochemicals, Oslo, Norway) and the sample group was divided in two subpopulations, one being positive on the CDT test (more than 6% CDT, n=25) and the other, negative (n=33).

Twenty-four samples were included of patients with either rheumatoid arthritis (n=8), ankylosing spondylitis (n=8) or Crohn's disease (n=8), diagnosed with these disorders in the Rheumatology Department of the University Hospital Ghent.

To establish reference values for the measured glycans, a control group of 60 blood donors (of which 26 female, average age of women was 60 years old, and of men was 59 years old) of which the health situation was compliant with Red Cross standards, was studied. These samples were obtained from the Transfusion Center of the Red Cross in Ghent, Belgium.

Etiologies, age and gender data are summarized in Table 1.

Serum Diagnostic Glycomics

Sample preparation procedure: 5 μl of the sera (215 in total) were incubated with 50 μl of RCM buffer (8 M urea, 360 mM Tris, pH 8.6, 3.2 mM EDTA) at 50° C. for one hour to denature the serum proteins. Subsequently, these mixtures were loaded in the wells of a Multiscreen-IP plate (Millipore, Bedford, Calif., USA), prepared as described previously (Papac et al., 1998). Reduction, iodoalkylation and deglycosylation steps were performed according to reported procedures (ibid.).

APTS derivatization reaction and cleanup: N-glycan derivatization with 8-amino-1,3,6-pyrenetrisulfonic acid and removal of excess free label were as described recently (Callewaert et al., 2001). Briefly, the deglycosylation mixture was evaporated to dryness and a 1 μl 1:1 mixture of 20 mM APTS (Molecular Probes, Eugene, Calif., USA) in 1.2 M citric acid and 1 M NaCNBH$_3$ in DMSO was added. The derivatization was allowed to proceed for 18 hours at 37° C. After this, the reaction was quenched by the addition of 10 μl of DI water. Excess un-reacted APTS was removed using a bed of Sephadex G10 packed in a Multiscreen filterplate (Millipore, Bedford, Calif., USA). After sample application, the resin beds were eluted three times by addition of 10 μl of water and a ten second centrifugation at 750×g in a table-top centrifuge equipped for handling 96-well plates (Eppendorf, Hamburg, Germany). The eluate was evaporated to dryness. After evaporation, the derivatized glycans were reconstituted in 5 μl of water.

Exoglycosidase digestion: 1 μl batches of the cleaned-up derivatized N-glycans were transferred to 250 μl PCR tubes or tapered-well microtiter plates for treatment with *Arthrobacter ureafaciens* sialidase (2 U/ml, Glyko, Novato, Calif.), overnight at 37° C. in 10 μl 20 mM sodium acetate pH 5.0. One unit of the sialidase is defined as the amount of enzyme that hydrolyzes one μmole of N-acetylneuraminosyl-D-lactose per minute at 25° C. and pH 5.0. After completion of the digestion, the samples were evaporated to dryness and reconstituted in 1 μl water.

Analysis by DNA-sequencer-adapted FACE: To each sample, 0.5 μl of the rhodamine-labeled Genescan™ 500 standard mixture (Perkin Elmer, Foster City, Calif., USA) and 1 μl of deionized formamide was added for internal referencing and to facilitate sample loading, respectively.

All experiments were performed on an Applied Biosystems 377A DNA-sequencer (Perkin Elmer, Foster City, Calif., USA), adapted for cooling as described (Callewaert et al., 2001). The 36 cm gel contained 10% of a 19:1 mixture of acrylamide:bisacrylamide (89 mM Tris, 89 mM borate, 2.2 mM EDTA). Prerunning was done at 3000 V for one hour. The electrophoresis voltage during separation was 3500 V and data were collected for three hours (separation of glycans up to 15 glucose units in size).

Data processing: Data analysis was performed using the Genescan 3.1 software (Applied Biosystems, Foster City, Calif., USA). We chose to use the heights of 14 well-defined peaks to obtain a numerical description of the profiles. This is a subset of the total number of observed peaks, because only those peaks were included that were quantifiable in all samples. We chose peak height rather than peak surface because the latter was more difficult to quantify in a routine way because of occasional extensive peak overlap. These data were assembled in MS Excell and further processed with the SPSS 10.0 statistics package (SPSS Inc., Chicago, Ill., USA). The assumption of normality of the variables over the studied populations was assessed using the Kolmogorov-Smirnov test at the 0.05 significance level. One-way parametric analysis of variance was followed by Tukey's Honestly Significant Difference and Scheffe's multiple comparison tests at 0.0001 significance level. Both Receiver Operating Curve (ROC) analysis and binary logistic regression were used to assess the classification efficiency of the potential diagnostic variables.

For figure preparation, all lanes on the same gel were aligned with the lane containing the APTS-labeled malto-oligosaccharide standard, using the positions of the peaks of the internal rhodamine-oligonucleotide standard. For clarity, the peaks corresponding to the rhodamine-labeled internal standards have been omitted after the alignment procedure.

Exoglycosidase Array Sequencing of the N-Glycan Pool

1 μl batches of APTS-labeled N-glycans, prepared as described under paragraph 8.2.2 were subjected to digestion with different mixtures of highly purified exoglycosidases. The identity of the mixtures is indicated in the figures and were combinations of the following treatments: *Arthrobacter ureafaciens* sialidase (2 U/ml, Glyko, Novato, Calif.); *Diplococcus pneumoniae* β-1,4-galactosidase (1U/ml, Boehringer, Mannheim, Germany); Jack bean β-N-acetylhexosaminidase (30 U/ml, Glyko, Novato, Calif., USA) and bovine epididymis α-fucosidase (0.5 U/ml, Glyko, Novato, Calif., USA). Unit definitions are as specified by the enzyme suppliers. After completion of the digestions, the samples were evaporated to dryness, reconstituted in 1 μl deionized water and analyzed on an ABI377 as described above.

TABLES

TABLE 1

| Details | | N | Group number | Age (years) | Sex (% male) |
|---|---|---|---|---|---|
| Healthy control | | 60 | 0 | 59.5 +/− 12.1 | 57 |
| HCC + cirrhosis | Alcoholism | 7 | 1 | 60.0 +/− 9.0 | 70 |
| | Chronic viral hepatitis | 9 | | | |
| Cirrhosis | Alcoholism | 8 | | | |
| | Chronic viral hepatitis | 11 | | | |
| | Autoimmune hepatits | 1 | | | |
| | Cryptogenic | 1 | | | |
| Chronic viral hepatitis | HBV | 5 | 2 | 44.6 +/− 17.3 | 60 |
| | HCV | 22 | | | |
| Non-HCC liver metastases | | 8 | 3 | 71.3 +/− 6.5 | 38 |
| Chronic alcoholism | CDT+ | 25 | 4 | N.A. | N.A. |
| | CDT− | 33 | 5 | | |
| Autoimmune diseases | Crohn's disease | 8 | 6 | 44.4 +/− 13.5 | 46 |
| | Ankylosing spondylitis | 8 | | | |
| | Rheumatoid arthritis | 8 | | | |

TABLE 2

Pearson correlation analysis (n = 214)

| | Peak 1 | Peak 2 | Peak 3 | Peak 7 | Peak 8 |
|---|---|---|---|---|---|
| Peak 1 | 1 | 0.845 | −0.802 | 0.418 | −0.596 |
| Peak 2 | | 1 | −0.81 | 0.551 | −0.609 |
| Peak 3 | | | 1 | −0.759 | 0.533 |
| Peak 7 | | | | 1 | −0.471 |
| Peak 8 | | | | | 1 |

All correlations are significant at the 0.00001 level (2-tailed)

TABLE 3

One-way analysis of variance over the 7 sample groups

| ANOVA | | Sum of Squares | df | Mean Square | F | Sig. |
|---|---|---|---|---|---|---|
| Log (Peak 1/Peak 8) | Between groups | 21.47 | 6 | 3.5787 | 49.3741 | 2.267E−37 |
| | Within groups | 15 | 207 | 0.0725 | | |
| | Total | 36.48 | 213 | | | |

TABLE 3-continued

| | | | | | | |
|---|---|---|---|---|---|---|
| Log (Peak 2/Peak 8) | Between groups | 44.39 | 6 | 7.399 | 58.0935 | 9.212E−42 |
| | Within groups | 26.36 | 207 | 0.1274 | | |
| | Total | 70.76 | 213 | | | |
| Log (Peak 7/Peak 8) | Between groups | 13.85 | 6 | 2.3084 | 46.7134 | 6.091E−36 |
| | Within groups | 10.23 | 207 | 0.0494 | | |
| | Total | 24.08 | 213 | | | |

Multiple comparison test results
Log (Peak 1/Peak 8)

| | Sample groups | N | Subset for alpha = .001 | |
|---|---|---|---|---|
| | | | 1 | 2 |
| Tukey's HSD | Controls | 60 | −0.0918 | |
| | CDT − alcoholism | 33 | −0.0184 | |
| | CDT + alcoholism | 25 | −0.0045 | |
| | Non-HCC liver metastases | 8 | 0.053 | |
| | Chronic hepatitis | 27 | 0.0631 | |
| | Auto-immune diseases | 24 | 0.1381 | |
| | cirrhosis | 37 | | 0.8128 |
| | Sig. | | 0.0688 | 1 |
| Scheffé's comparison | Controls | 60 | −0.0918 | |
| | CDT − alcoholism | 33 | −0.0184 | |
| | CDT + alcoholism | 25 | −0.0045 | |
| | Non-HCC liver metastases | 8 | 0.053 | |
| | Chronic hepatitis | 27 | 0.0631 | |
| | Auto-immune diseases | 24 | 0.1381 | |
| | cirrhosis | 37 | | 0.8128 |
| | Sig. | | 0.2413 | 1 |

Log (Peak 2/Peak 8)

| | Sample groups | N | Subset for alpha = .001 | | |
|---|---|---|---|---|---|
| | | | 1 | 2 | 3 |
| Tukey's HSD | Controls | 60 | −1.0926 | | |
| | CDT − alcoholism | 33 | −0.9803 | −0.9803 | |
| | CDT + alcoholism | 25 | −0.9537 | −0.9537 | |
| | Auto-immune diseases | 24 | −0.8616 | −0.8616 | |
| | Non-HCC liver metastases | 8 | −0.7223 | −0.7223 | |
| | Chronic hepatitis | 27 | | −0.5947 | |
| | cirrhosis | 37 | | 0.8128 | 0.204 |
| | Sig. | | 0.0103 | 0.0062 | 1 |
| Scheffé's comparison | Controls | 60 | −1.0926 | | |
| | CDT − alcoholism | 33 | −0.9803 | | |
| | CDT + alcoholism | 25 | −0.9537 | | |
| | Auto-immune diseases | 24 | −0.8616 | | |
| | Non-HCC liver metastases | 8 | −0.7223 | | |
| | Chronic hepatitis | 27 | −0.5947 | | |
| | cirrhosis | 37 | | 0.204 | |
| | Sig. | | 0.0022 | 1 | |

Log (Peak 7/Peak 8)

| | Sample groups | N | Subset for alpha = .001 | |
|---|---|---|---|---|
| | | | 1 | 2 |
| Tukey's HSD | Auto-immune diseases | 24 | −0.1435 | |
| | Controls | 60 | −0.1406 | |
| | Non-HCC liver metastases | 8 | −0.0848 | |
| | Chronic hepatitis | 27 | −0.0212 | |
| | CDT − alcoholism | 33 | −0.0076 | |
| | CDT + alcoholism | 25 | 0.0258 | |
| | cirrhosis | 37 | | 0.5798 |
| | Sig. | | 0.1491 | 1 |
| Scheffé's comparison | Auto-immune diseases | 24 | −0.1435 | |
| | Controls | 60 | −0.1406 | |
| | Non-HCC liver metastases | 8 | −0.0848 | |
| | Chronic hepatitis | 27 | −0.0212 | |
| | CDT − alcoholism | 33 | −0.0076 | |
| | CDT + alcoholism | 25 | 0.0258 | |
| | cirrhosis | 37 | | 0.5798 |
| | Sig. | | 0.3845 | 1 |

Means for groups in homogeneous subsets are displayed

REFERENCES

1. Adam, B. L., Vlahou, A., Semmes, O. J. and Wright, G. L., Jr. (2001) Proteomic approaches to biomarker discovery in prostate and bladder cancers, Proteomics, 1, 1264-1270.
2. Anton, R. F. (2001) Carbohydrate-deficient transferrin for detection and monitoring of sustained heavy drinking. What have we learned? Where do we go from here?, Alcohol, 25, 185-188.
3. Aoyagi, Y., Suzuki, Y., Igarashi, K., Saitoh, A., Oguro, M., Yokota, T., Mori, S., Suda, T., Isemura, M. and Asakura, H. (1993) Carbohydrate structures of human alpha-fetoprotein of patients with hepatocellular carcinoma: presence of fucosylated and non-fucosylated triantennary glycans, Br J Cancer, 67, 486-492.
4. Ashwell, G. and Harford, J. (1982) Carbohydrate-specific receptors of the liver, Annu Rev Biochem, 51, 531-554.
5. Ashwell, G. and Steer, C. J. (1981) Hepatic recognition and catabolism of serum glycoproteins, Jama, 246, 2358-2364.
6. Burgess, J. B., Baenziger, J. U. and Brown, W. R. (1992) Abnormal surface distribution of the human asialoglycoprotein receptor in cirrhosis, Hepatology, 15, 702-706.
7. Byrn, R., Thomas, P., Medrek, P., Spigelman, Z. and Zamcheck, N. (1984) Modified radioassay for measuring asialoglycoprotein in serum, Clin Chem, 30, 1692-1696.
8. Callewaert, N., Geysens, S., Molemans, F. and Contreras, R. (2001) Ultrasensitive profiling and sequencing of N-linked oligosaccharides using standard DNA-sequencing equipment, Glycobiology, 11, 275-281.
9. Dell, A. and Morris, H. R. (2001) Glycoprotein structure determination by mass spectrometry, Science, 291, 2351-2356.
10. Eto, T. and Takahashi, H. (1999) Enhanced inhibition of hepatitis B virus production by asialoglycoprotein receptor-directed interferon, Nat Med, 5, 577-581.
11. Fracanzani, A. L., Burdick, L., Borzio, M., Roncalli, M., Bonelli, N., Borzio, F., Maraschi, A., Fiorelli, G. and Fargion, S. (2001) Contrast-enhanced Doppler ultrasonography in the diagnosis of hepatocellular carcinoma and premalignant lesions in patients with cirrhosis, Hepatology, 34, 1109-1112.
12. Fung, E. T., Wright, G. L., Jr. and Dalmasso, E. A. (2000) Proteomic strategies for biomarker identification: progress and challenges, Curr Opin Mol Ther, 2, 643-650.
13. Granovsky, M., Fata, J., Pawling, J., Muller, W. J., Khokha, R. and Dennis, J. W. (2000) Suppression of tumor growth and metastasis in Mgat5-deficient mice, Nature Medicine, 6, 306-312.
14. Guile, G. R., Rudd, P. M., Wing, D. R., Prime, S. B. and Dwek, R. A. (1996) A rapid high-resolution high-perfor- 15. Ha-Kawa, S. K., Tanaka, Y., Hasebe, S., Kuniyasu, Y., Koizumi, K., Ishii, Y., Yamamoto, K., Kashiwagi, T., Ito, A., Kudo, M., Ikekubo, K., Tsuda, T. and Murase, K. (1997) Compartmental analysis of asialoglycoprotein receptor scintigraphy for quantitative measurement of liver function: a multicentre study, Eur J Nucl Med, 24, 130-137.

16. Hirabayashi, J., Arata, Y. and Kasai, K. (2001) Glycome project: concept, strategy and preliminary application to *Caenorhabditis elegans*, Proteomics, 1, 295-303.

17. Ikeda, Y. and Taniguchi, N. (2001) Enzymatic properties and biological functions of beta 1,4-N-acetylglucosaminyltransferase III, Trends in Glycoscience and Glycotechnology, 13, 167-176.

18. Ise, H., Sugihara, N., Negishi, N., Nikaido, T. and Akaike, T. (2001) Low asialoglycoprotein receptor expression as markers for highly proliferative potential hepatocytes, Biochem Biophys Res Commun, 285, 172-182.

19. Ishibashi, K., Nishikawa, A., Hayashi, N., Kasahara, A., Sato, N., Fujii, S., Kamada, T. and Taniguchi, N. (1989) N-Acetylglucosaminyltransferase-Iii in Human-Serum, and Liver and Hepatoma Tissues—Increased Activity in Liver-Cirrhosis and Hepatoma Patients, Clinica Chimica Acta, 185, 325-332.

20. Johnson, P. J., Poon, T. C., Hjelm, N. M., Ho, C. S., Blake, C. and Ho, S. K. (2000) Structures of disease-specific serum alpha-fetoprotein isoforms, Br J Cancer, 83, 1330-1337.

21. Johnston-Wilson, N. L., Bouton, C. M., Pevsner, J., Breen, J. J., Torrey, E. F. and Yolken, R. H. (2001) Emerging technologies for large-scale screening of human tissues and fluids in the study of severe psychiatric disease, Int J Neuropsychopharmacol, 4, 83-92.

22. Kang, R., Ikeda, Y., Miyoshi, E., Wang, W., Li, W., Ihara, Y., Sheng, Y. and Taniguchi, N. (2000) Cell cycle-dependent regulation of N-acetylglucosaminyltransferase-III in a human colon cancer cell line, Colo201, Arch Biochem Biophys, 374, 52-58.

23. Kellner, R. (2000) Proteomics. Concepts and perspectives, Fresenius J Anal Chem, 366, 517-524.

24. Kitada, T., Miyoshi, E., Noda, K., Higashiyama, S., Ihara, H., Matsuura, N., Hayashi, N., Kawata, S., Matsuzawa, Y. and Taniguchi, N. (2001) The addition of bisecting N-acetylglucosamine residues to E-cadherin down-regulates the tyrosine phosphorylation of beta-catenin, Journal of Biological Chemistry, 276, 475-480.

25. Kobata, A. (2000) A journey to the world of glycobiology, Glycoconj J, 17, 443-464.

26. Kuper, H., Ye, W., Broome, U., Romelsjo, A., Mucci, L. A., Ekbom, A., Adami, H. O., Trichopoulos, D. and Nyren, O. (2001) The risk of liver and bile duct cancer in patients with chronic viral hepatitis, alcoholism, or cirrhosis, Hepatology, 34, 714-718.

27. Marshall, J. S., Green, A. M., Pensky, J., Williams, S., Zinn, A. and Carlson, D. M. (1974) Measurement of circulating desialylated glycoproteins and correlation with hepatocellular damage, J Clin Invest, 54, 555-562.

28. Martin, K., Talukder, R., Hay, F. C. and Axford, J. S. (2001) Characterization of changes in IgG associated oligosaccharide profiles in rheumatoid arthritis, psoriatic arthritis, and ankylosing spondylitis using fluorophore linked carbohydrate electrophoresis, J Rheumatol, 28, 1531-1536.

29. Matsumoto, K., Maeda, Y., Kato, S. and Yuki, H. (1994) Alteration of asparagine-linked glycosylation in serum transferrin of patients with hepatocellular carcinoma, Clin Chim Acta, 224, 1-8.

30. Miki, K., Kubota, K., Inoue, Y., Vera, D. R. and Makuuchi, M. (2001) Receptor measurements via Tc-GSA kinetic modeling are proportional to functional hepatocellular mass, J Nucl Med, 42, 733-737.

31. Miyoshi, E., Ihara, Y., Hayashi, N., Fusamoto, H., Kamada, T. and Taniguchi, N. (1995) Transfection of N-acetylglucosaminyltransferase III gene suppresses expression of hepatitis B virus in a human hepatoma cell line, HB611, J Biol Chem, 270, 28311-28315.

32. Miyoshi, E., Ihara, Y., Nishikawa, A., Saito, H., Uozumi, N., Hayashi, N., Fusamoto, H., Kamada, T. and Taniguchi, N. (1995) Gene expression of N-acetylglucosaminyltransferases III and V: a possible implication for liver regeneration, Hepatology, 22, 1847-1855.

33. Miyoshi, E., Nishikawa, A., Ihara, Y., Gu, J. G., Sugiyama, T., Hayashi, N., Fusamoto, H., Kamada, T. and Taniguchi, N. (1993) N-Acetylglucosaminyltransferase-Iii and N-Acetylglucosaminyltransferase-V Messenger-Rna Levels in Lec Rats During Hepatocarcinogenesis, Cancer Research, 53, 3899-3902.

34. Miyoshi, E., Nishikawa, A., Ihara, Y., Hayashi, N., Fusamoto, H., Kamada, T. and Taniguchi, N. (1994) Selective Suppression of N-Acetylglucosaminyltransferase-Iii Activity in a Human Hepatoblastoma Cell-Line Transfected with Hepatitis-B Virus, Cancer Research, 54, 1854-1858.

35. Miyoshi, E., Noda, K., Ko, J. H., Ekuni, A., Kitada, T., Uozumi, N., Ikeda, Y., Matsuura, N., Sasaki, Y., Hayashi, N., Hori, M. and Taniguchi, N. (1999) Overexpression of alpha 1-6 fucosyltransferase in hepatoma cells suppresses intrahepatic metastasis after splenic injection in athymic mice, Cancer Research, 59, 2237-2243.

36. Mori, S., Aoyagi, Y., Yanagi, M., Suzuki, Y. and Asakura, H. (1998) Serum N-acetylglucosaminyltransferase III activities in hepatocellular carcinoma, Journal of Gastroenterology and Hepatology, 13, 610-619.

37. Nakagawa, H., Kawamura, Y., Kato, K., Shimada, I., Arata, Y. and Takahashi, N. (1995) Identification of neutral and sialyl N-linked oligosaccharide structures from human serum glycoproteins using three kinds of high-performance liquid chromatography, Anal Biochem, 226, 130-138.

38. Noda, K., Miyoshi, E., Uozumi, N., Yanagidani, S., Ikeda, Y., Gao, C., Suzuki, K., Yoshihara, H., Yoshikawa, K., Kawano, K., Hayashi, N., Hori, M., Taniguchi, N. and Yoshikawa, M. (1998) Gene expression of alpha 1-6 fucosyltransferase in human hepatoma tissues: a possible implication for increased fucosylation of alpha-fetoprotein, Hepatology, 28, 944-952.

39. Noda, K., Miyoshi, E., Uozumi, N., Yanagidani, S., Ikeda, Y., Gao, C. X., Suzuki, K., Yoshihara, H., Yoshikawa, M., Kawano, K., Hayashi, N., Hori, M. and Taniguchi, N. (1998) Gene expression of alpha 1-6 fucosyltransferase in human hepatoma tissues: A possible implication for increased fucosylation of alpha-fetoprotein, Hepatology, 28, 944-952.

40. Opanasopit, P., Shirashi, K., Nishikawa, M., Yamashita, F., Takakura, Y. and Hashida, M. (2001) In vivo recognition of mannosylated proteins by hepatic mannose receptors and mannan-binding protein, Am J Physiol Gastrointest Liver Physiol, 280, G879-889.

41. Pandey, A. and Mann, M. (2000) Proteomics to study genes and genomes, Nature, 405, 837-846.

42. Papac, D. I., Briggs, J. B., Chin, E. T. and Jones, A. J. (1998) A high-throughput microscale method to release N-linked oligosaccharides from glycoproteins for matrix-assisted laser desorption/ionization time-of-flight mass spectrometric analysis, Glycobiology, 8, 445-454.

43. Paweletz, C. P., Trock, B., Pennanen, M., Tsangaris, T., Magnant, C., Liotta, L. A. and Petricoin, E. F., 3rd (2001) Proteomic patterns of nipple aspirate fluids obtained by SELDI-TOF: potential for new biomarkers to aid in the diagnosis of breast cancer, Dis Markers, 17, 301-307.

44. Petricoin, E. F., Ardekani, A. M., Hitt, B. A., Levine, P. J., Fusaro, V. A., Steinberg, S. M., Mills, G. B., Simone, C., Fishman, D. A., Kohn, E. C. and Liotta, L. A. (2002) Use of proteomic patterns in serum to identify ovarian cancer, Lancet, 359, 572-577.

45. Roseman, S. (2001) Reflections on glycobiology, J Biol Chem, 276, 41527-41542.

46. Saitoh, A., Aoyagi, Y. and Asakura, H. (1993) Structural analysis on the sugar chains of human alpha 1-antitrypsin: presence of fucosylated biantennary glycan in hepatocellular carcinoma, Arch Biochem Biophys, 303, 281-287.

47. Salas-Solano, O., Schmalzing, D., Koutny, L., Buonocore, S., Adourian, A., Matsudaira, P. and Ehrlich, D. (2000) Optimization of high-performance DNA sequencing on short microfabricated electrophoretic devices, Anal Chem, 72, 3129-3137.

48. Sawamura, T., Nakada, H., Hazama, H., Shiozaki, Y., Sameshima, Y. and Tashiro, Y. (1984) Hyperasialoglycoproteinemia in patients with chronic liver diseases and/or liver cell carcinoma. Asialoglycoprotein receptor in cirrhosis and liver cell carcinoma, Gastroenterology, 87, 1217-1221.

49. Taniguchi, N., Ekuni, A., Ko, J. H., Miyoshi, E., Ikeda, Y., Ihara, Y., Nishikawa, A., Honke, K. and Takahashi, M. (2001) A glycomic approach to the identification and characterization of glycoprotein function in cells transfected with glycosyltransferase genes, Proteomics, 1, 239-247.

50. Taniguchi, N., Miyoshi, E., Ko, J. H., Ikeda, Y. and Ihara, Y. (1999) Implication of N-acetylglucosaminyltransferases III and V in cancer: gene regulation and signaling mechanism, Biochimica Et Biophysica Acta-Molecular Basis of Disease, 1455, 287-300.

51. Verma, M., Wright, G. L., Jr., Hanash, S. M., Gopal-Srivastava, R. and Srivastava, S. (2001) Proteomic approaches within the NCI early detection research network for the discovery and identification of cancer biomarkers, Ann N Y Acad Sci, 945, 103-115.

52. Wang, W., Li, W., Ikeda, Y., Miyagawa, J. I., Taniguchi, M., Miyoshi, E., Sheng, Y., Ekuni, A., Ko, J. H., Yamamoto, Y., Sugimoto, T., Yamashita, S., Matsuzawa, Y., Grabowski, G. A., Honke, K. and Taniguchi, N. (2001) Ectopic expression of alpha 1,6 fucosyltransferase in mice causes steatosis in the liver and kidney accompanied by a modification of lysosomal acid lipase, Glycobiology, 11, 165-174.

53. Wassler, M. J., Foote, C. I., Gelman, I. H. and Shur, B. D. (2001) Functional interaction between the SSeCKS scaffolding protein and the cytoplasmic domain of beta1, 4-galactosyltransferase, J Cell Sci, 114, 2291-2300.

54. Wassler, M. J. and Shur, B. D. (2000) Clustering of cell surface (beta)1,4-galactosyltransferase I induces transient tyrosine phosphorylation of focal adhesion kinase and loss of stress fibers, J Cell Sci, 113, 237-245.

55. Watson, M., Rudd, P. M., Bland, M., Dwek, R. A. and Axford, J. S. (1999) Sugar printing rheumatic diseases: a potential method for disease differentiation using immunoglobulin G oligosaccharides, Arthritis Rheum, 42, 1682-1690.

56. Wuyts, B., Delanghe, J. R., Kasvosve, I., Wauters, A., Neels, H. and Janssens, J. (2001) Determination of carbohydrate-deficient transferrin using capillary zone electrophoresis, Clin Chem, 47, 247-255.

57. Yamashita, K., Koide, N., Endo, T., Iwaki, Y. and Kobata, A. (1989) Altered glycosylation of serum transferrin of patients with hepatocellular carcinoma, J Biol Chem, 264, 2415-2423.

58. Yoshimura, M., Ihara, Y., Matsuzawa, Y. and Taniguchi, N. (1996) Aberrant glycosylation of E-cadherin enhances cell-cell binding to suppress metastasis, J Biol Chem, 271, 13811-13815.

59. Yoshimura, M., Nishikawa, A., Ihara, Y., Taniguchi, S. and Taniguchi, N. (1995) Suppression of Lung Metastasis of B16 Mouse Melanoma by N-Acetylglucosaminyltransferase-Iii Gene Transfection, Proceedings of the National Academy of Sciences of the United States of America, 92, 8754-8758.

60. Zhang, S. W., Fu, X. Y., Cao, S. L., Shen, Z. H. and Gu, J. X. (1999) Down-regulation of beta1,4-galactosyltransferase gene expression by cell-cycle suppressor gene p16, Biochim Biophys Acta, 1444, 49-54.

61. Zhang, S. W., Lin, W. S., Ying, X. L., Zhu, D., Guo, M. Y. and Gu, J. X. (2000) Effect of suppression of TGF-beta1 expression on cell-cycle and gene expression of beta-1,4-galactosyltransferase 1 in human hepatocarcinoma cells, Biochem Biophys Res Commun, 273, 833-838.

What is claimed is:

1. A method of detecting liver damage that is accompanied by formation of regenerative liver nodules in a mammal, said method comprising: obtaining a sample of serum or blood plasma from the mammal, said sample containing
   a pool of the total serum or blood N-linked glycoproteins;
   generating a first N-linked carbohydrate profile, wherein said first N-linked carbohydrate profile represents the diversity and concentration of carbohydrate moieties present in the pool of total serum or blood N-linked glycoproteins;
   quantifying, in the first N-linked carbohydrate profile, an amount of at least one N-linked carbohydrate moiety;
   comparing the quantified amount of said at least one N-linked carbohydrate moiety with a quantified amount of said same at least one N-linked carbohydrate moiety in other N-linked carbohydrate profiles representing the diversity and concentration of carbohydrate moieties of a pool of total serum or blood N-linked glycoproteins derived from serum or plasma samples from mammals not suffering from liver damage; and
   attributing differences between the quantified amount of said at least one N-linked carbohydrate moiety and the quantified amount of said same at least one N-linked carbohydrate moiety in other N-linked carbohydrate profiles liver damage that is accompanied by formation of regenerative liver nodules.

2. The method according to claim 1, wherein said at least one N-linked carbohydrate moiety is selected from the group consisting of:
   GlcNAc(β-1,2)Man(α-1,3)[GlcNAc(β-1,2)Man(α-1,6)]Man(β-1, 4)GlcNAc(β-1,4)[Fuc(α-1,6)]GlcNAc (glycan 1),
   GlcNAc(β-1,2)Man(α-1,3)[GlcNAc(β-1,4)][GlcNAc(β-1,2)Man(α-1,6)]Man(β-1,4)GlcNAc(β-1,4) [Fuc(α1,6)]GlcNAc(glycan 2), Gal(β-1,4)GlcNAc(β-1,2)Man(α-1,3) [Gal(β-1,4)GlcNAc(β-1,2)Man(α-1,6)]Man(β-1,4)GlcNAc(β-1,4)GlcNAc(glycan 3), Gal(β-1,4)GlcNAc(β-1,2)Man(α-1,3)[GlcNAc(β-1,4)][Gal(β-1,4)GlcNAc(β-1,2)Man(α-1,6)]Man(β-1,4)GlcNAc(β-1,4)[Fuc(α-1,6)]GlcNAc(glycan 7), Gal(β-1,4)GlcNAc(β-1,2)[Gal(β-1,4)GlcNAc(β-1,4)]Man(α1,3)[Gal(β-(β-1, 4) GlcNAc(β-1,2)Man(α-1,6)]Man(β-1,4)GlcNAc(β-1,4)GlcNAc(glycan 8), a fragment derived of glycan 1, 2, 3, 7 or 8, a sialylated derivative of glycan 1, 2, 3, 7 or 8, and a feature of glycan 1, 2, 3, 7 or 8 or derivative or fragment thereof.

3. The method according to claim 2 wherein the mammal is a human.

4. The method of detecting liver damage that is accompanied by formation of regenerative liver nodules in a mammal according to claim 3, further comprising observing other quantitative or qualitative indications of the mammal's physical condition.

5. The method according to claim 1, wherein said differences between the quantified amount of said at least one N-linked carbohydrate moiety and the quantified amount of said same at least one N-linked carbohydrate moiety in the other N-linked carbohydrate profiles is measured as a difference in amounts of glycan 1 and glycan 8, and/or glycan 2 and glycan 8, and/or glycan 7 and glycan 8, and/or glycan 1 and glycan 3, and/or glycan 2 and glycan 3, and/or glycan 7 and glycan 3.

6. The method according to claim 3 wherein the mammal is a human.

7. The method according to claim 1 wherein the mammal is a human.

8. The method of detecting liver damage that is accompanied by formation of regenerative liver nodules in a mammal according to claim 1, further comprising observing other quantitative or qualitative indications of the mammal's physical condition.

9. A method of detecting the presence or the predisposition of hepatocellular carcinoma in a mammal suffering from liver damage that is accompanied by formation of regenerative liver nodules, said method comprising:

obtaining a sample of serum or blood plasma from the mammal, said sample containing a pool of total serum or blood N-linked glycoproteins;

generating a first N-linked carbohydrate profile, wherein said first N-linked carbohydrate profile represents the diversity and concentration of carbohydrate moieties present in the pool of total serum or blood N-linked glycoproteins;

quantifying, in the first N-linked carbohydrate profile, an amount of at least one N-linked carbohydrate moiety;

comparing the quantified amount of said at least one N-linked carbohydrate moiety with a quantified amount of said same at least one N-linked carbohydrate moiety in other N-linked carbohydrate profiles representing the diversity and concentration of carbohydrate moieties of a pool of total serum or blood N-linked glycoproteins derived from serum or plasma samples from mammals suffering from said liver damage but free of hepatocellular carcinoma; and attributing differences between said quantified amount of said at least one N-linked carbohydrate moiety and the quantified amount of said same at least one N-linked carbohydrate moiety in said other N-linked carbohydrate profiles to the presence, or predisposition of hepatocellular carcinoma.

10. The method of claim 9 wherein comparing the quantified amount of said at least one carbohydrate moiety with a quantified amount of said same at least one N-linked carbohydrate moiety in other carbohydrate profiles comprises comparing differences in amounts of Gal(β-1,4)GlcNAc(β-1,2)Man(α-1,3)[GlcNAc(β-1,4)][Gal(β-1,4)GlcNAc (β-1,2)Man(α-1,6)]Man(β-1,4)GlcNAc(β-1,4)[Fuc(α-1,6)]GlcNAc(glcycan 7) and a product of N-acetylgluosaminyl-transferase V (glycan 14).

* * * * *

UNITED STATES PATENT AND TRADEMARK OFFICE
CERTIFICATE OF CORRECTION

PATENT NO. : 7,335,512 B2
APPLICATION NO. : 10/968579
DATED : February 26, 2008
INVENTOR(S) : Nico L. M. Callewaert and Roland H. Contreras Page 1 of 1

It is certified that error appears in the above-identified patent and that said Letters Patent is hereby corrected as shown below:

On the title page:
In ITEM (73) Assignees:      change "Interubiversitair" to --Interuniversitair--

In the claims:
CLAIM 1, COLUMN 34, LINE 57,      change "profiles liver" to --profiles to liver--
CLAIM 2, COLUMN 35, LINE 8,      change "Man($\alpha$1,3)[Gal($\beta$-($\beta$-1, 4) GlcNAc" to --Man($\alpha$-1,3)[Gal($\beta$-1,4)GlcNAc--
CLAIM 6, COLUMN 35, LINE 30,      change "claim 3" to --claim 5--
CLAIM 10, COLUMN 36, LINE 35,      change "[GlcNAc($\beta$-1,4)[]Gal($\beta$-1,4)" to --[GlcNAc($\beta$-1,4)][Gal($\beta$-1,4)--

Signed and Sealed this
Sixteenth Day of April, 2013

Teresa Stanek Rea
*Acting Director of the United States Patent and Trademark Office*